(12) United States Patent
Chin et al.

(10) Patent No.: US 7,875,031 B2
(45) Date of Patent: Jan. 25, 2011

(54) SYSTEM AND METHOD FOR IMPLANTING SPINAL STABILIZATION DEVICES

(75) Inventors: Kingsley Richard Chin, Philadelphia, PA (US); Matthew Ibarra, Lakewood, CA (US)

(73) Assignee: Spinefrontier, LLS, Philadelphia, PA (US)

( * ) Notice: Subject to any disclaimer, the term of this patent is extended or adjusted under 35 U.S.C. 154(b) by 775 days.

(21) Appl. No.: 11/557,541

(22) Filed: Nov. 8, 2006

(65) Prior Publication Data

US 2007/0073294 A1 Mar. 29, 2007

Related U.S. Application Data

(63) Continuation-in-part of application No. 10/669,927, filed on Sep. 24, 2003, now Pat. No. 7,282,064.

(60) Provisional application No. 60/737,666, filed on Nov. 17, 2005.

(51) Int. Cl.
*A61B 17/70* (2006.01)

(52) U.S. Cl. .................. 606/86 A; 606/279; 606/99

(58) Field of Classification Search ............... 606/86 A, 606/86 R, 99, 104, 246, 250–253, 279, 54, 606/56, 59, 80, 96; 408/69, 87–102
See application file for complete search history.

(56) References Cited

U.S. PATENT DOCUMENTS

| | | | | |
|---|---|---|---|---|
| 3,628,535 A | * | 12/1971 | Ostrowsky et al. | .......... 604/303 |
| 5,374,267 A | * | 12/1994 | Siegal | .......... 606/250 |
| 6,368,320 B1 | * | 4/2002 | Le Couedic et al. | .......... 606/250 |
| 6,769,434 B2 | * | 8/2004 | Liddicoat et al. | .......... 128/898 |
| 2004/0106922 A1 | * | 6/2004 | Snyder | .......... 606/62 |
| 2004/0138662 A1 | * | 7/2004 | Landry et al. | .......... 606/61 |
| 2004/0172022 A1 | * | 9/2004 | Landry et al. | .......... 606/61 |
| 2005/0215999 A1 | | 9/2005 | Birkmeyer et al. | |
| 2006/0111712 A1 | | 5/2006 | Jackson | |
| 2006/0167454 A1 | | 7/2006 | Ludwig et al. | |

* cited by examiner

*Primary Examiner*—Eduardo C Robert
*Assistant Examiner*—Steven J Cotroneo
(74) *Attorney, Agent, or Firm*—AKC Patents LLC; Aliki K. Collins

(57) ABSTRACT

A system and a method for providing minimally invasive access to the spine of a patient and implanting spinal stabilization devices. The system utilizes one or more post-type access devices. The post-type access device includes a cage with an aperture and two or more posts extending from the cage and being removably attached to the cage. The posts are supported at the top of the access device by a support ring structure. A pedicle screw is inserted into the access device and through the cage aperture and the screw-access device assembly is inserted into an opening of the patient's body. The base aperture is dimensioned to securely support the head of the screw. Side openings between the posts allow the insertion and placement of stabilization devices, such as rods, wires, or plates from almost any direction.

7 Claims, 31 Drawing Sheets

300 

```
┌─────────────────────────────────────────────────────────────────────────┐
│  Perform small skin incisions on the patient's body to form skin openings  302 │
└─────────────────────────────────────────────────────────────────────────┘
┌─────────────────────────────────────────────────────────────────────────┐
│  Insert guide wires through the skin openings into the tissue and the bones │
│               and anchor them in the pathology areas        304            │
└─────────────────────────────────────────────────────────────────────────┘
┌─────────────────────────────────────────────────────────────────────────┐
│  Use solid tissue dilators over the guide wires to develop deep channels   │
│          from the skin openings to the pathology areas     306             │
└─────────────────────────────────────────────────────────────────────────┘
┌─────────────────────────────────────────────────────────────────────────┐
│           Slide hollow dilators over the solid dilators        308        │
└─────────────────────────────────────────────────────────────────────────┘
┌─────────────────────────────────────────────────────────────────────────┐
│  Remove solid dilators                                           310      │
└─────────────────────────────────────────────────────────────────────────┘
┌─────────────────────────────────────────────────────────────────────────┐
│  Tap the pedicles with the pedicle screw tap                     312      │
└─────────────────────────────────────────────────────────────────────────┘
┌─────────────────────────────────────────────────────────────────────────┐
│  Remove the tap and screw in the pedicle screw and cage  314              │
└─────────────────────────────────────────────────────────────────────────┘
┌─────────────────────────────────────────────────────────────────────────┐
│  Insert post wires inside the hollow dilator and into the cage bores 316  │
└─────────────────────────────────────────────────────────────────────────┘
┌─────────────────────────────────────────────────────────────────────────┐
│  Insert posts along the post wires and screw them into the bores 317      │
└─────────────────────────────────────────────────────────────────────────┘
┌─────────────────────────────────────────────────────────────────────────┐
│       Place support ring and snap-ring supports on the posts    318       │
└─────────────────────────────────────────────────────────────────────────┘
┌─────────────────────────────────────────────────────────────────────────┐
│              Remove hollow dilators             319                       │
└─────────────────────────────────────────────────────────────────────────┘
┌─────────────────────────────────────────────────────────────────────────┐
│              Remove guide wires                 320                       │
└─────────────────────────────────────────────────────────────────────────┘
┌─────────────────────────────────────────────────────────────────────────┐
│              Remove post wires                  321                       │
└─────────────────────────────────────────────────────────────────────────┘
┌─────────────────────────────────────────────────────────────────────────┐
│  Dissect and cut the fascia between the posts of the access devices   322 │
└─────────────────────────────────────────────────────────────────────────┘
┌─────────────────────────────────────────────────────────────────────────┐
│     Insert rod between the channels formed by the posts      323          │
└─────────────────────────────────────────────────────────────────────────┘
┌─────────────────────────────────────────────────────────────────────────┐
│       Push down rod with the pusher and seat in the cage base  324        │
└─────────────────────────────────────────────────────────────────────────┘
┌─────────────────────────────────────────────────────────────────────────┐
│         Tighten set screws onto the cage to secure the rod 325            │
└─────────────────────────────────────────────────────────────────────────┘
┌─────────────────────────────────────────────────────────────────────────┐
│         Remove support ring and snap rings from the posts 326             │
└─────────────────────────────────────────────────────────────────────────┘
┌─────────────────────────────────────────────────────────────────────────┐
│         Unscrew and remove posts;  Close incisions            327         │
└─────────────────────────────────────────────────────────────────────────┘
```

FIG. 9

SYSTEM AND METHOD FOR IMPLANTING SPINAL STABILIZATION DEVICES

CROSS REFERENCE TO RELATED CO-PENDING APPLICATIONS

This application is a continuation in part of U.S. application Ser. No. 10/669,927 filed on Sep. 24, 2003 and entitled APPARATUS AND METHOD FOR CONNECTING SPINAL VERTEBRAE the contents of which are expressly incorporated herein by reference. This application also claims the benefit of U.S. provisional application Ser. No. 60/737,666 filed on Nov. 17, 2005 and entitled "SYSTEM AND METHOD FOR IMPLANTING SPINAL STABILIZATION DEVICES", the contents of which are expressly incorporated herein by reference.

FIELD OF THE INVENTION

The present invention relates to a system and a method for implanting spinal stabilization devices, and more particularly to a system and a method that allow the percutaneous transfer of connecting devices and instruments within one access channel or between two or more adjacent access channels placed deep in two or more locations of the patient's body, respectively.

BACKGROUND OF THE INVENTION

It is well known that traditional surgical procedures in locations deep within a patient's body require a long incision, extensive muscle stripping, prolonged retraction of muscles for visualization, and denervation and devascularization of the adjacent tissue. These procedures result in extensive tissue traumatization and consequently in prolonged recovery time, risk of infections, high hospitalization costs, pain that can be more severe than the pain due to the initial ailment, and in some cases permanent scarring. The current state of the art for minimally invasive surgical procedures utilizes cylindrical tubes, cannulas, or blades to access locations deep in the patient's body. The use of these access devices rather than a long incision causes fewer traumas to the adjacent tissue, reduces the recovery time and pain and may be performed in some cases under only local anesthesia. The potential for the avoidance of general anesthesia reduces post-operative recovery time and the risk of complications.

Minimally invasive surgical procedures are especially desirable for spine surgeries because spine pathologies are located deep within the body without clear muscle planes and there is danger of damaging the adjacent neural and vascular tissues. In treating the majority of spinal pathologies, the spinal muscles are stripped from the bony elements of the spine followed by laminectomy or discectomy to expose the dura, the nerve roots, and the discs. The incision has to be wide enough and the tissues have to be retracted to maintain a channel from the skin to the floor of the spinal canal that will allow direct visualization. Laminectomy or discectomy is usually followed by spine stabilization or fusion. Spine stabilization involves implantation of pedicle screws in the pedicles and securing of rods or plates to the pedicles screws, as described in U.S. Pat. No. 6,626,909, the contents of which are incorporated herein by reference. The destruction to the spinal structures is even more extensive during the spine stabilization procedures, which require more lateral tissue dissection and exposure to access the transverse processes and pedicles for placement of pedicle screws, rod constructs for stability, and bone graft under direct vision.

Furthermore, in spine stabilization procedures, connecting elements, such as rods, plates or wires are placed and fixed between two or more locations of the spine. Placement of these connecting elements requires open surgery, which is currently one of the major limitations of other percutaneous access methodologies. Accordingly there is a need for inserting and placing these connecting elements between two or more separate spinal locations without performing open surgery. The emerging percutaneous access systems that address some of the limitations of open surgeries are limited to cylindrical tubes, cannulas, or blades. One of the shared limitations of these systems is that they all have solid walls which in our experience tend to reduce visualization of the deep structures and require specific alignment of a predefined access slot. Accordingly, there is a need for a percutaneous access system that allows visualization of the deep structures and does not require specific alignment.

SUMMARY OF THE INVENTION

In general, in one aspect, the invention features a system for providing access to a spine of a patient. The system comprises a post-type access device insertable into a first location of the patient's spine. The post-type access device includes a cage, at least two elongated posts and a support element. The cage includes a bottom portion configured to receive a bone fixation element and prevent the bone fixation element from passing entirely therethrough and two side portions extending from the bottom portion parallel to each other and forming a channel configured to receive a spine stabilization element and a locking element. Receipt of the locking element by the side portions causes locking of the relative positions of the bone fixation element and the stabilization element. The elongated posts extend from the side portions and are arranged to permit passage of the stabilization element along a direction transverse to a central axis of the access device. The support element is configured to be attached to proximal ends of the elongated post.

Implementations of this aspect of the invention may include one or more of the following features. The system may further include one or more additional post-type access devices insertable into the patient's spine in locations adjacent to the first location. The bone fixation element may be a polyaxial screw. The spine stabilization element may be rods, plates, wires, vertebral disc replacements, nuclear replacements, facet arthroplasty devices, dynamic stabilization devices, interbody fusion devices, or articulating versions thereof. The bone fixation elements may be screws, hooks, loops, pins, nuts, washers, wires, sutures, and staples. The support element may be a support ring or a support semi-ring. The elongated posts are arranged to permit passage of objects along the transverse direction or the central axis. The objects may be carrier devices, surgical instruments, medical devices, fixation devices, vertebral disc replacement devices, facet arthroplasty devices, vertebral element replacement devices, interbody devices, fixation tools, connecting devices, connecting tools, tissue, grafting material, or illumination devices. The system may further include a semi-ring configured to be attached to and connect the elongated posts along a direction transverse to the central axis.

In general, in another aspect, the invention features a method for performing percutaneous minimally invasive spinal surgery on a patient by inserting a first post-type access device into a first location of the patient's spine and then inserting a second post-type access device into a second location of the patient's spine. Each of the post-type access device includes a cage, at least two elongated posts and a support element. The cage includes a bottom portion configured to receive a bone fixation element and prevent the bone fixation element from passing entirely therethrough and two side portions extending from the bottom portion parallel to each other and forming a channel configured to receive a spine stabilization element and a locking element. Receipt of the locking element by the side portions causes locking of the relative positions of the bone fixation element and the stabilization element. The elongated posts extend from the side portions and are arranged to permit passage of the stabilization element along a direction transverse to a central axis of the access device. The support element is configured to be attached to proximal ends of the elongated post.

Implementations of this aspect of the invention may include one or more of the following features. The method may further include attaching the cages of the first and second post-type access devices to first and second bone locations of the patient's spine via the bone fixation elements, respectively. Next, dissecting and cutting the fascia between the posts of the first and second post-type access devices. Next, inserting the stabilization element into the channels of the first and second post-type access devices, the stabilization element extending from the first to the second post type access device in a direction transverse to their central axes, and then locking the position of the stabilization element relative to the bone fixation elements via the locking elements. The method may also include removing the support rings and the posts from the first and second post-type access devices. The step of inserting may include making a first incision on a first location of the patient's skin, and then advancing a first guide wire through the first incision, through tissue underlying the first skin location and into the first underlying spine location. Next, forming a first body cavity around the first guide wire via a solid dilator, the cavity extending from the first skin location to the first underlying spine location and then sliding a hollow dilator over the solid dilator and then removing the solid dilator. The step of attaching includes tapping the first underlying spine location with a screw tap and then removing the screw tap, then inserting the bone fixation element into the cage and then inserting the cage with the bone fixation element through the hollow dilator and attaching the bone fixation element and cage to the first underlying spine location. Next, inserting at least two elongated posts through the hollow dilator wherein the post comprise proximal ends and distal ends and extend from the first underlying spine location to the first skin location, then attaching the distal ends of the posts to the side portions and then attaching a support ring to the proximal ends of the elongated posts. Finally, removing the hollow dilators and the first guide wire. The method may further include inserting a second stabilization element into channels of a third and fourth post-type access devices, wherein the third and fourth access devices are inserted in third and fourth locations of the patient's spine adjacent to the first and second locations and wherein the second stabilization rod is arranged parallel to the first stabilization rod. The method may also include inserting a third stabilization rod wherein the third stabilization rod cross-links the first and second stabilization rods and is arranged transverse to the first and second stabilization rods. The cage may further include a second channel arranged perpendicular to the first channel and is configured to receive the third stabilization element. The access devices may be preassembled prior to inserting them into locations of the patient's spine or may be assembled after inserting them into locations of the patient's spine.

Among the advantages of this invention may be one or more of the following. The invention provides novel devices and methods for improving percutaneous surgeries for all applications and approaches in the body that previously required open surgery. These improvements will be beneficial to both patients and surgeons in that this invention will reduce the technical difficulty of these operations, improve visualization, decrease risks of iatrogenic injuries to vital structures, decrease length of hospitalization and associated costs, decrease operative time, decrease recovery time, and decrease postoperative pain.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views:

FIG. 9 is a block diagram of the spinal surgical procedure according to one embodiment of this invention;

DETAILED DESCRIPTION OF THE INVENTION

The present invention relates to a system and a method for placing spinal stabilization devices into a patient's back via minimally invasive surgery (MIS).

Figure 1:
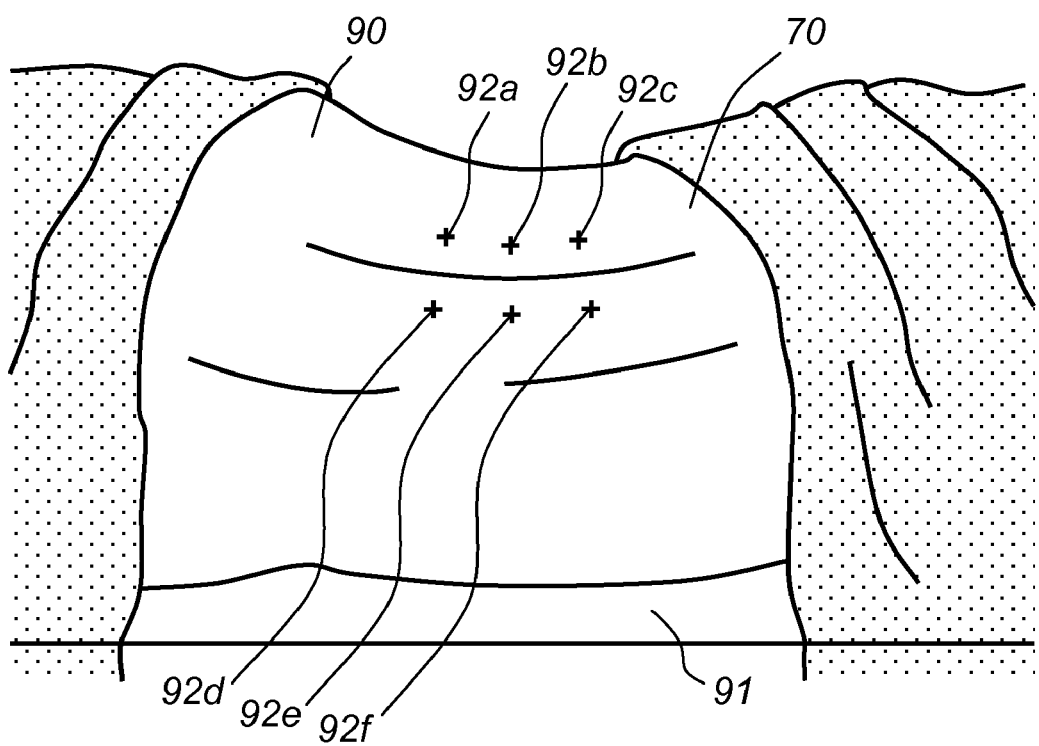
FIG. 1 is a top view of the back of a patient positioned prone on the operating table in preparation for spinal surgery.
Figure 2:
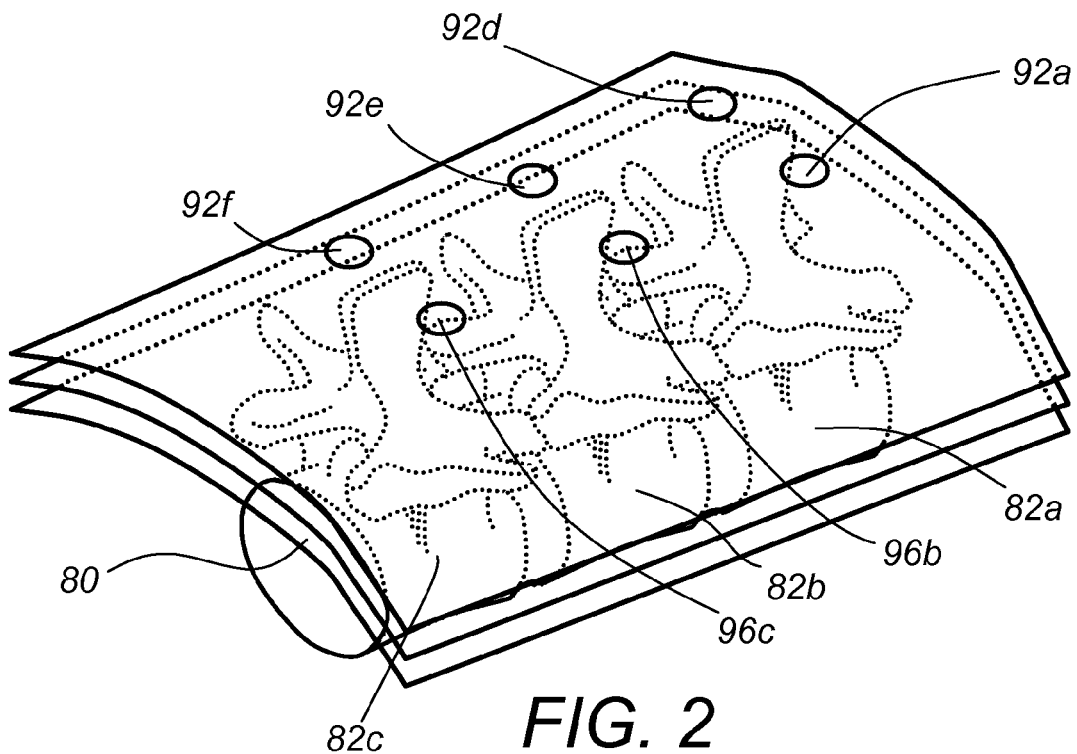
FIG. 2 is a layered top view of the patient's back with incisions made on the skin extending through the lumbodorsal fascia to the deep tissues.
Figure 3:
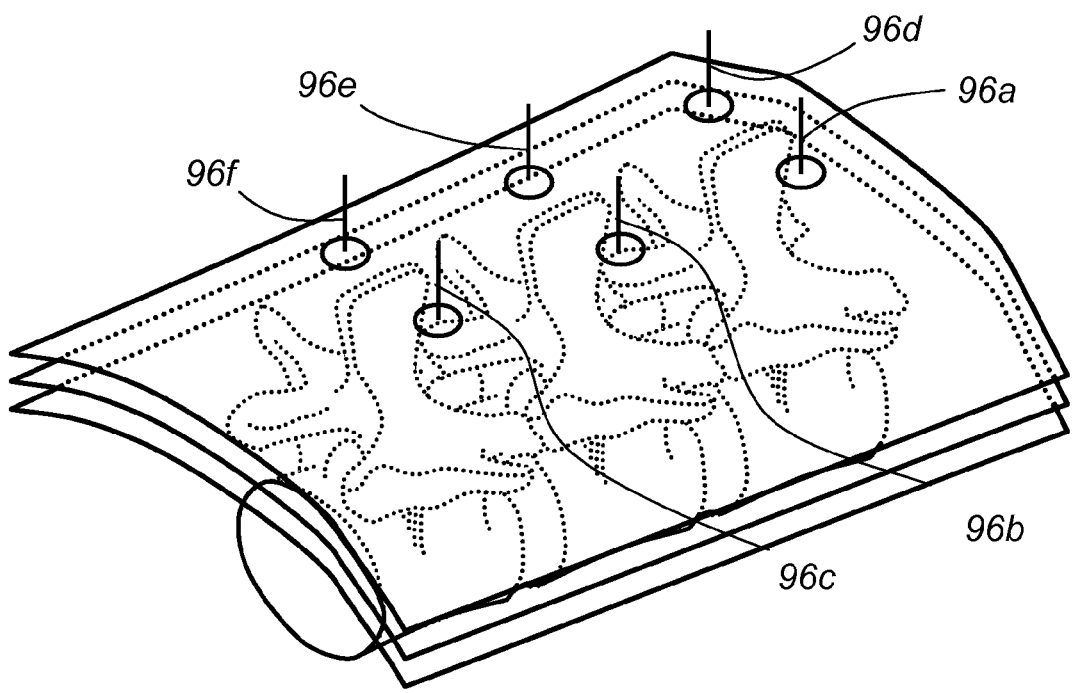
FIG. 3 is a layered top view of the patient's back with incisions on the skin and guide K-wires placed percutaneously through the skin and into the underlying vertebrae.
Figure 4:
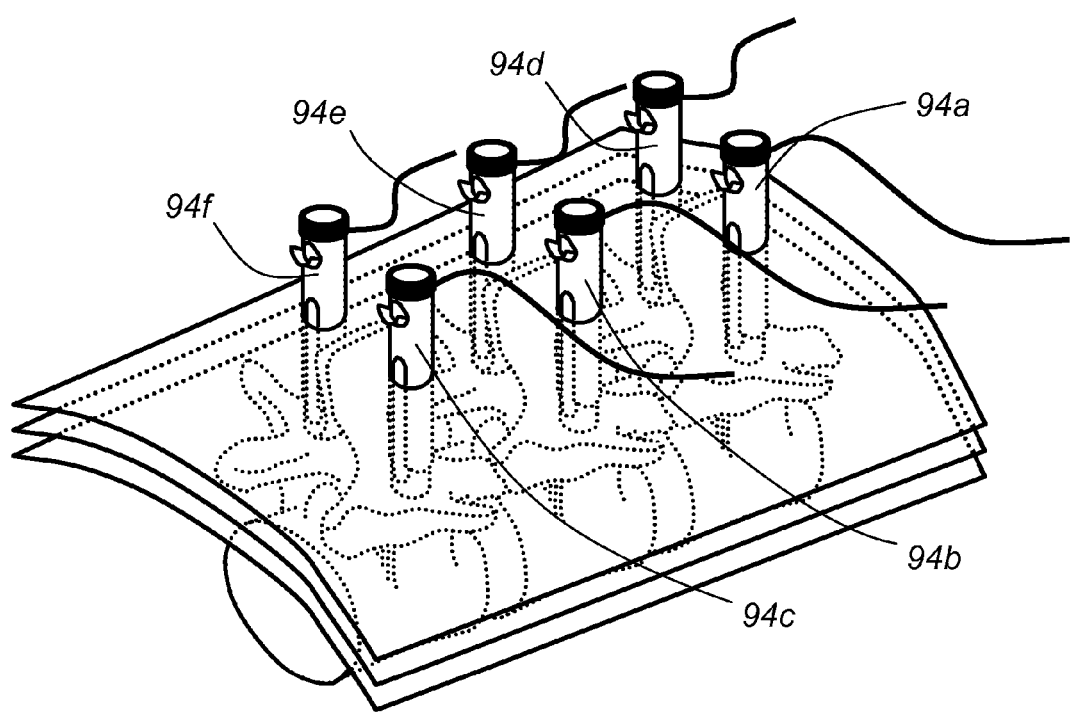
FIG. 4 is a top view of the patient's back with access devices placed in the openings formed from the skin surface and extending deep into the pathology areas.

Referring to FIG. 1, a patient 90 is positioned prone, lying flat on an operating table 91 in preparation for a minimally invasive surgery. Locations 92a-92f are marked on the patient's lower back corresponding to underlying pedicle locations of adjacent vertebrae 82a, 82b, 82c, respectively, and incisions are made on the marked areas, as shown in FIG. 2. The incisions extend through the lumbodorsal fascia to the deep tissues. Next, guide K-wires 96a-96f are inserted through the openings formed by the incisions and are placed in contact with the underlying pedicles, as shown in FIG. 3. For MIS procedures the tissue around the K-wires is dilated and access devices are inserted around the locations of the K-wires leading to the underlying pedicles, shown in FIG. 4. For spinal stabilization procedures, pedicle screws are inserted through the access devices and are attached to the underlying pedicles. Stabilizing connecting rods or plates are placed between the adjacent vertebrae and are attached to the pedicles via the pedicle screws.

Figure 5:
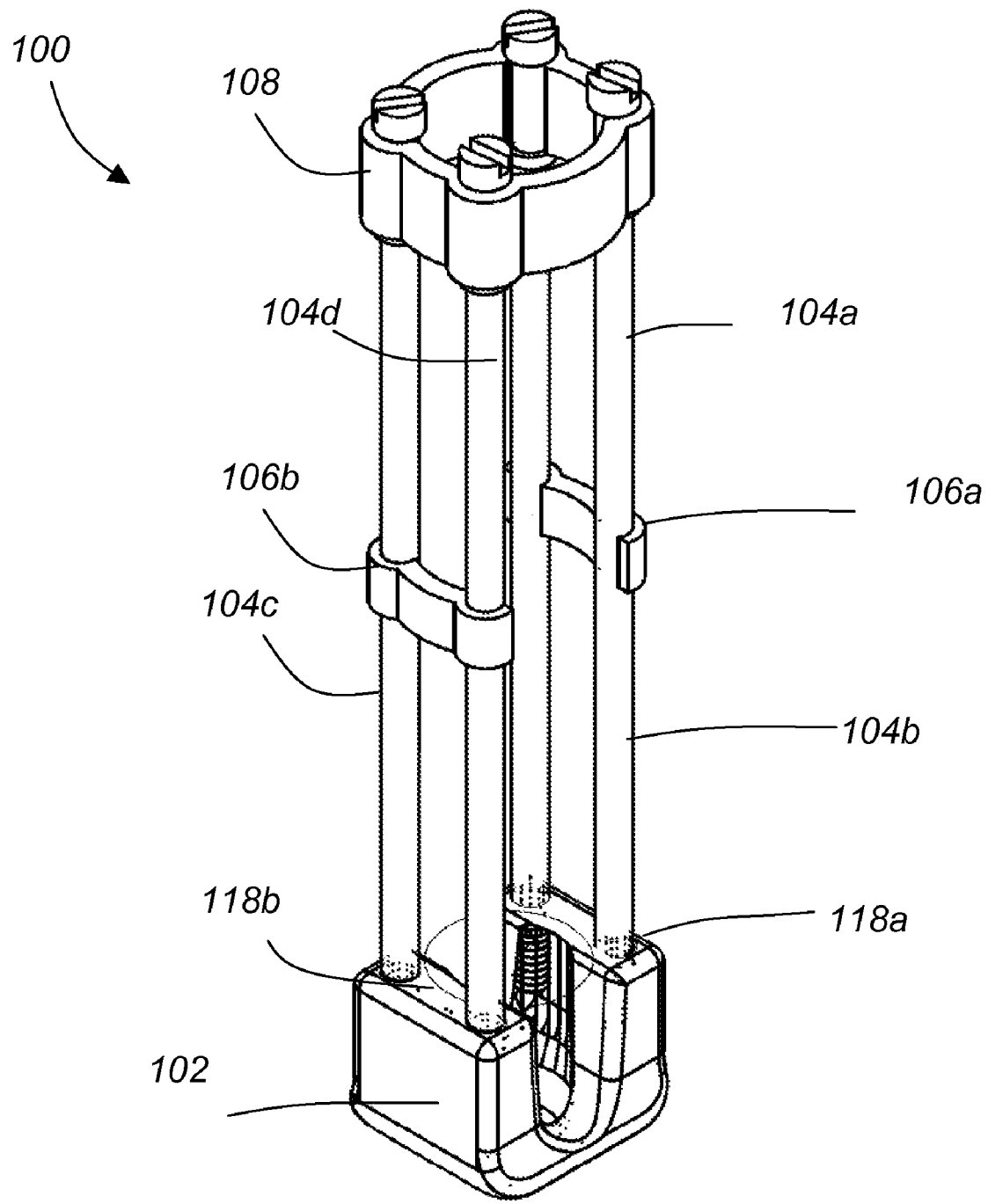
FIG. 5 is a perspective view of an access device according to one embodiment of this invention.
Figure 6:
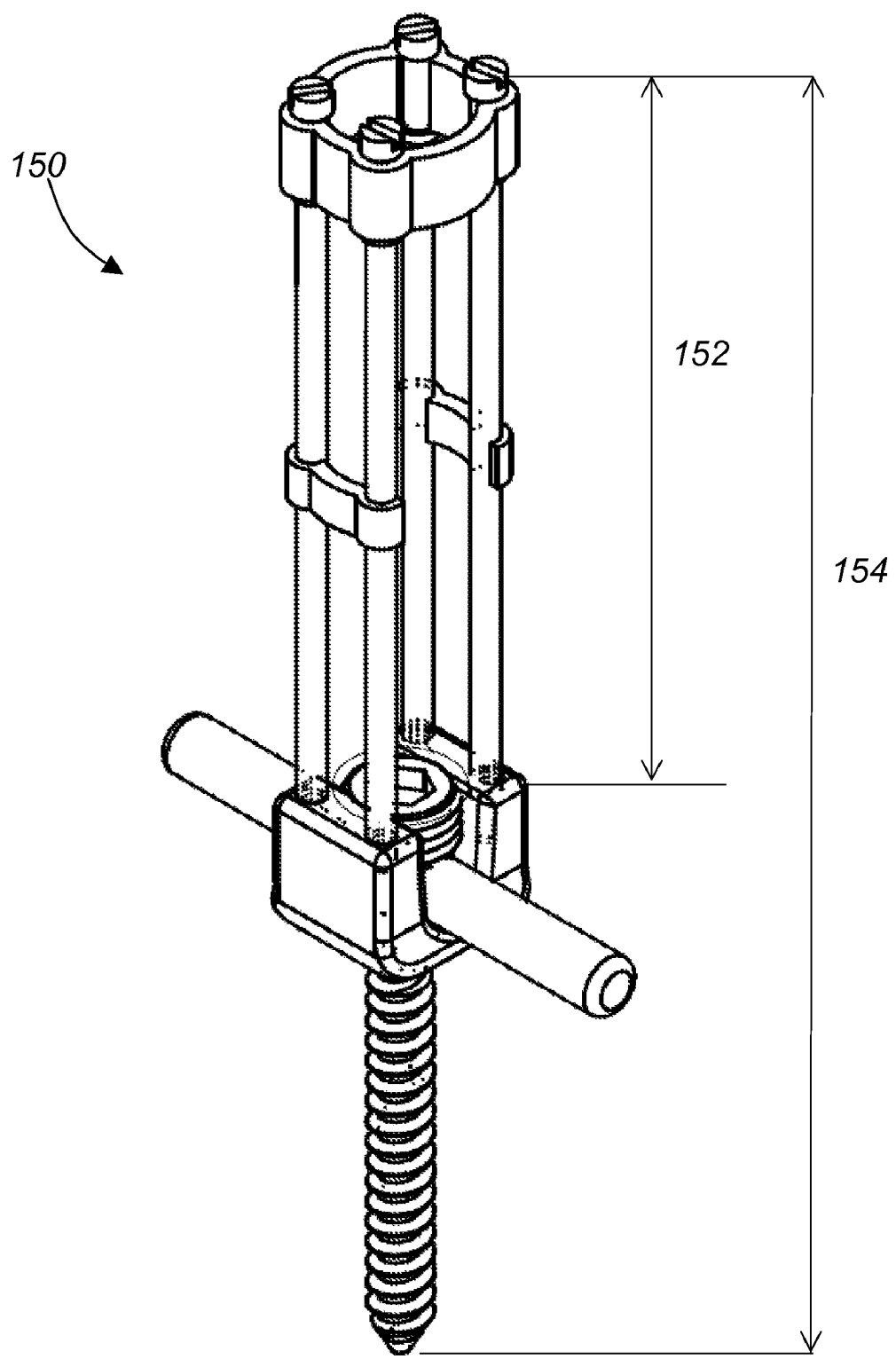
FIG. 6 is a perspective view of an access device assembly including the access device of FIG. 5, a pedicle screw and a portion of a connecting rod.
Figure 7:
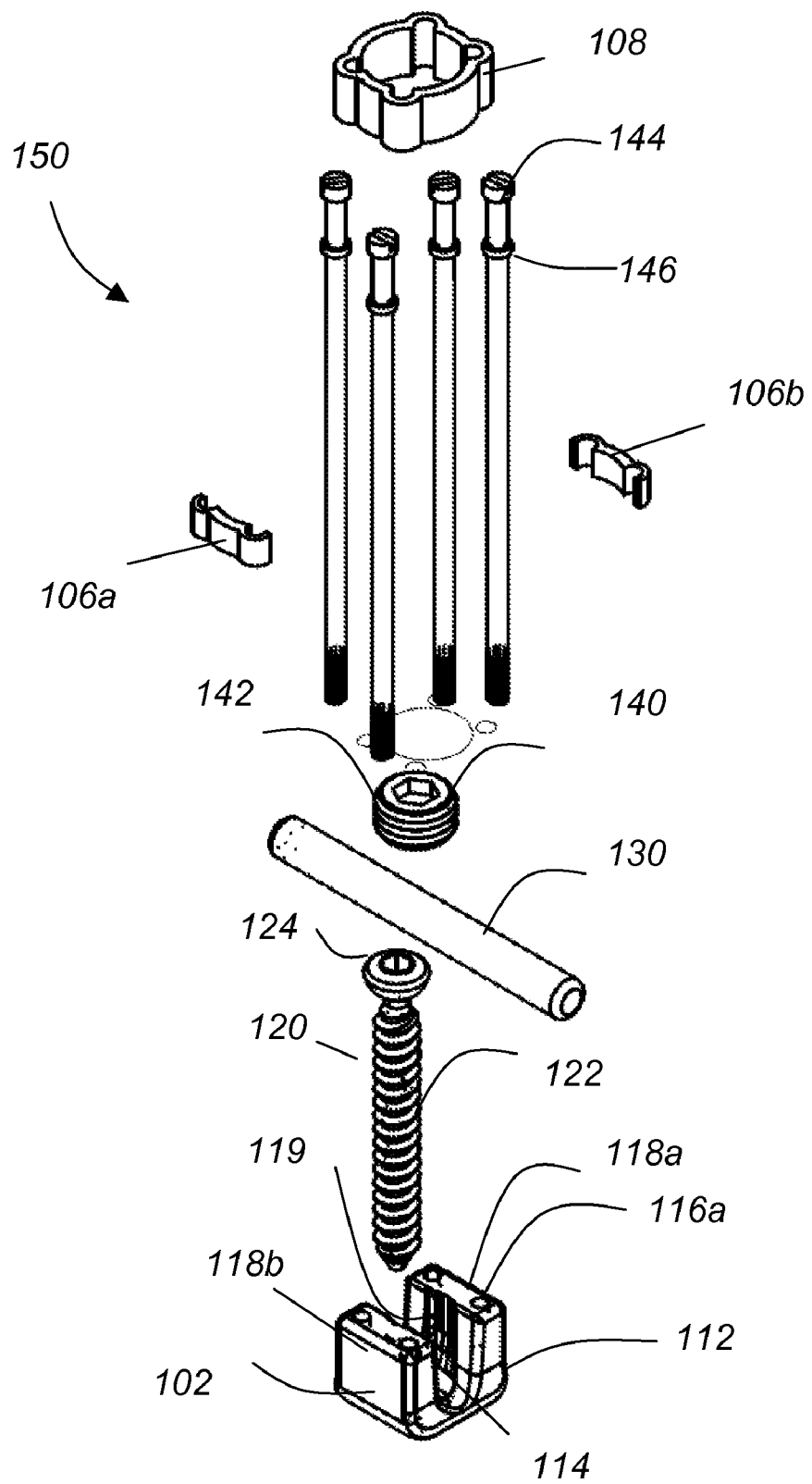
FIG. 7 is an exploded perspective view of the access device assembly of FIG. 6.

According to one embodiment of this invention a post-type access device assembly allows the insertion and attachment of pedicle screws to the underlying pedicles and the insertion of connecting rods or plates from and into almost any direction. Referring to FIG. 5, FIG. 6 and FIG. 7 a post-type access device 100 includes a cage 102, four posts 104a, 104b, 104c and 104d, a support ring 108 and two snap semi-rings 106a, 106b. The four posts 104a-104d are threaded into four threaded bores 116a-116d of the cage 102, respectively. The support ring 108 attaches to the top of the four posts 104a-104d and helps to hold the four posts together. The two snap semi-rings 106a, 106b attach to two adjacent posts and provide additional support for the post-type access device. The top end of each post has a recess 144 for receiving a screwdriver. Each post also has a stop ring 146 for preventing the support ring 108 from sliding downwards. The support ring 108 may have a circular or rectangular cross section. The two semi-rings 106a, 106b may be semi-circular or straight. The cage 102 has a base 112 in which an aperture 114 is formed. The aperture is dimensioned so that a threaded portion 122 of the pedicle screw 120 may be inserted through the aperture 114, while a head 124 of the pedicle screw 120 rests on a concave semispherical surface of the base 112. The head 124 may be polyaxially rotatable within the base 112. The cage 102 also has a pair of arms 118a, 118b, extending from the base 112, generally parallel to each other. Each of the arms 118a and 118b has two of the threaded bores 116a, 116d and 116b, 116c, respectively. The inside surfaces 119a, 119b, of the arms 118a, 118b, respectively, are threaded for receiving a set screw 140. After attaching the pedicle screw 120 to the underlying pedicle, a rod 130 is inserted and placed between the arms 118a, 118b. The set screw 140 is then threaded on top of the rod and into the threaded inner surfaces of the arms 118a, 118b of the cage 102, thereby pressing and securing the rod to the cage and the pedicle screw 120. The set screw 140 has a hexagonal recess for receiving a screwdriver. The outside surface of the set screw has threads that are dimensioned to engage with the threads of the inside surfaces of the arms 118a, 118b of the cage 102. The height 152 of the access device is in the range of 5 cm to 20 cm. The posts 104a-104d may have a length in the range of 5 cm to 25 cm. The height of the entire access device assembly may in the range of 5 cm to 25 cm.

Figure 8:
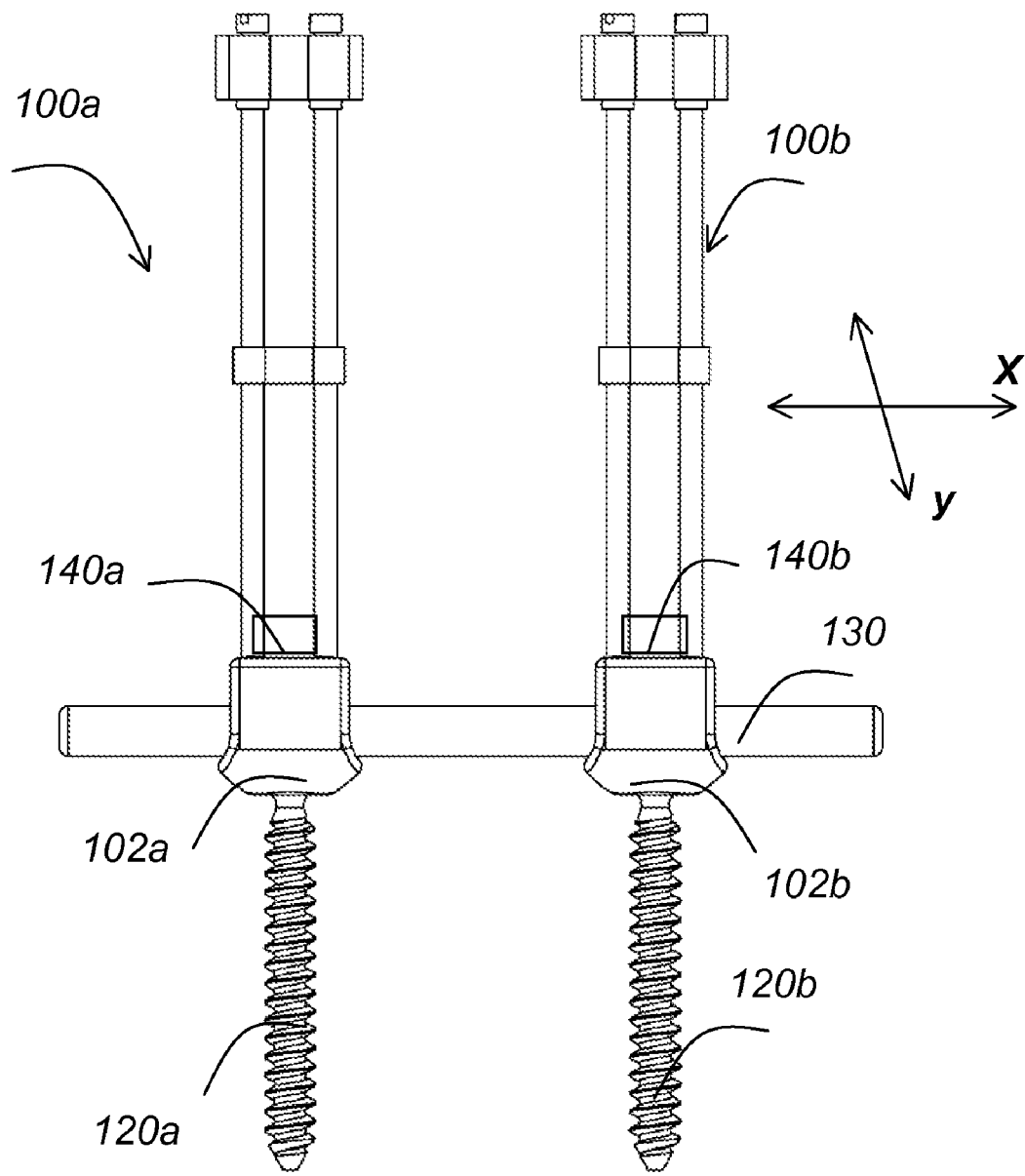
FIG. 8 is a perspective view of two access device assemblies of FIG. 6 connected via a connecting rod.

For inserting the pedicle screw 120 into the pedicle, first the screw 120 is inserted through the base aperture 114 of the cage 102 and then the access device-pedicle screw assembly is inserted into the pedicle area and the screw is attached to the pedicle with a screwdriver. Next, the rod 130 is inserted through the channels formed between the posts 104a-104d of adjacent access devices 100a, 100b and is placed in between the arms of each cage 102a, 102b, respectively, shown in FIG. 8. Next the set screws 140a, 140b, are attached to the cages 102a, 102b, respectively, thereby securing the rod in the x-direction. In other embodiments, a second rod may be inserted through the channel formed in the y-direction and then secured between the arms of cage 102b and a third cage placed adjacent to cage 102b in the y-direction (not shown).

Figure 10:
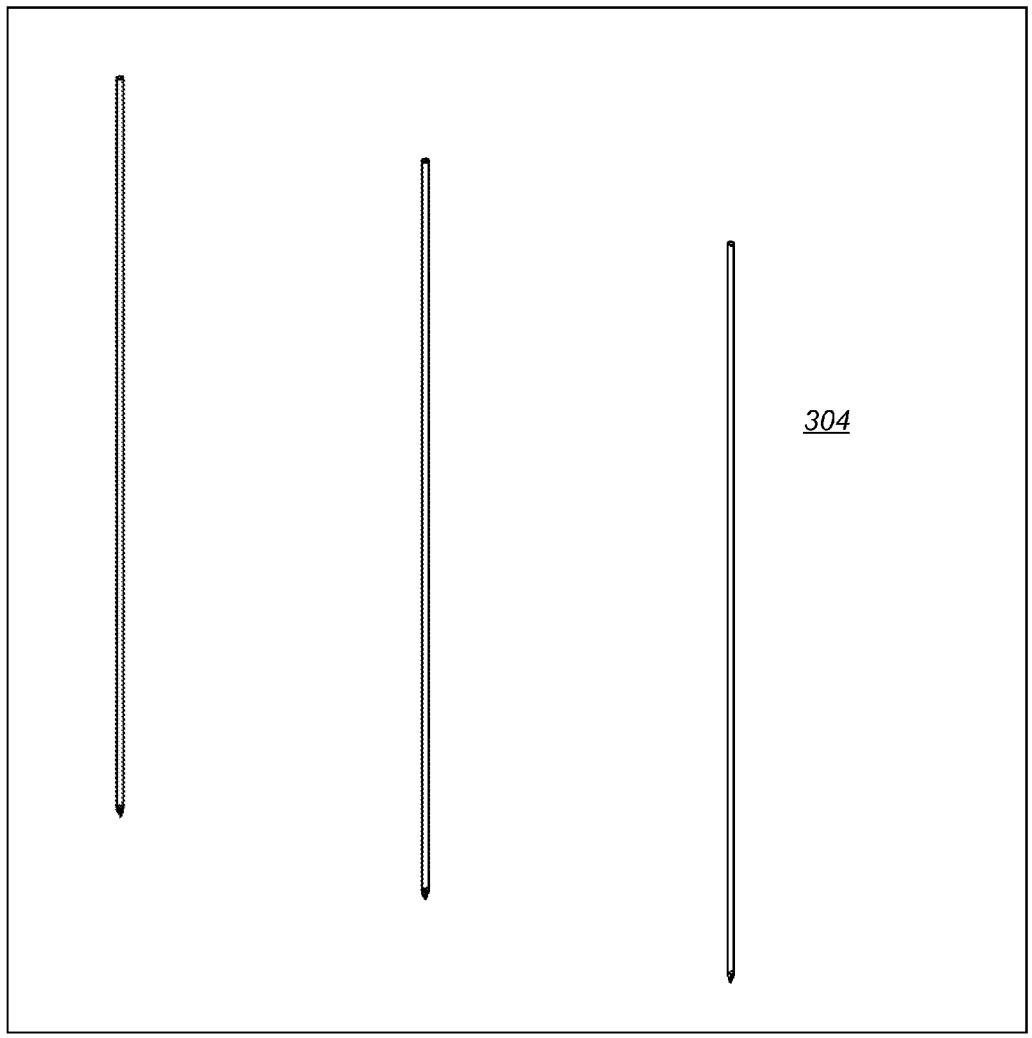
FIG. 10 is a schematic diagram of step 304 of the procedure of FIG. 9 depicting a perspective view of three guide K-wires in isolation, as positioned in the pedicles of three adjacent vertebras.
Figure 11:
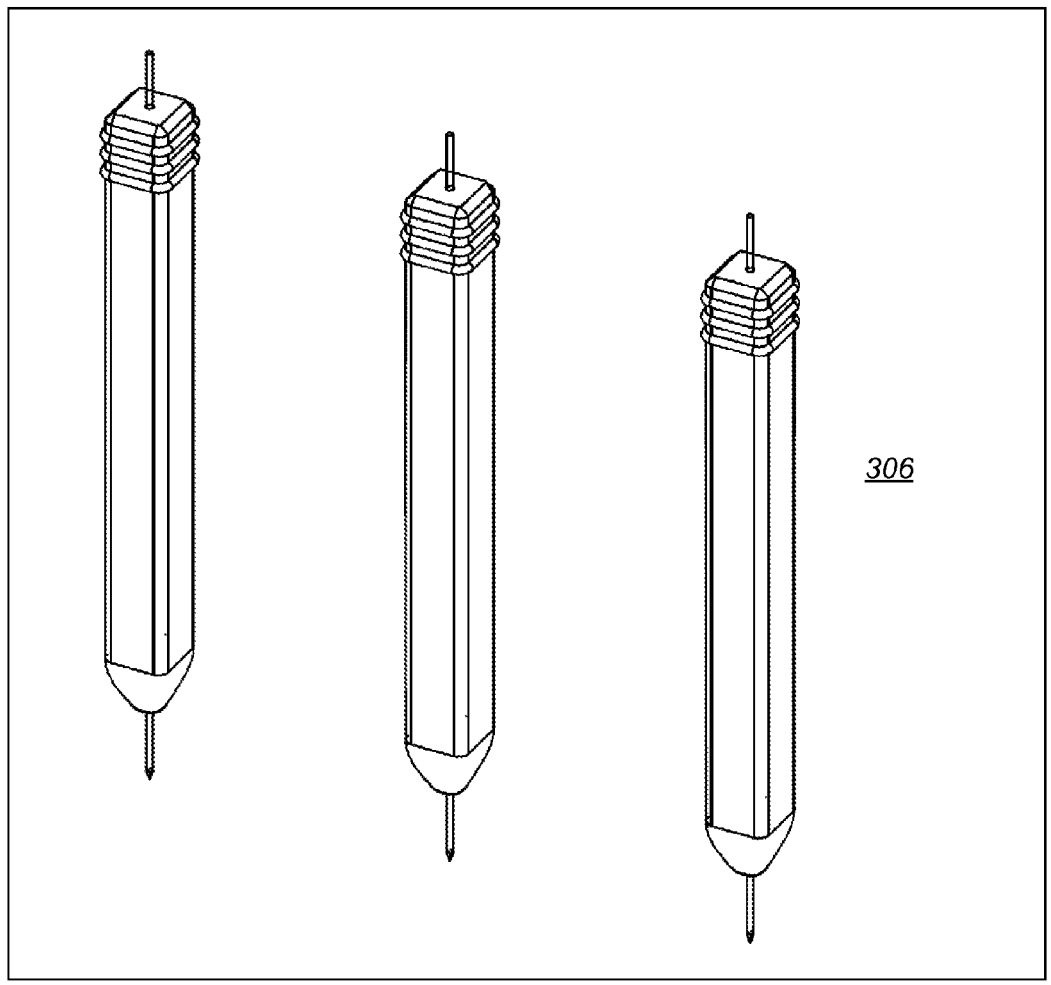
FIG. 11 is a schematic diagram of step 306 of the procedure of FIG. 9 depicting a perspective view of the three guide K-wires with solid dilators advanced along the guide wires for dilating the surrounding soft tissue.
Figure 12:
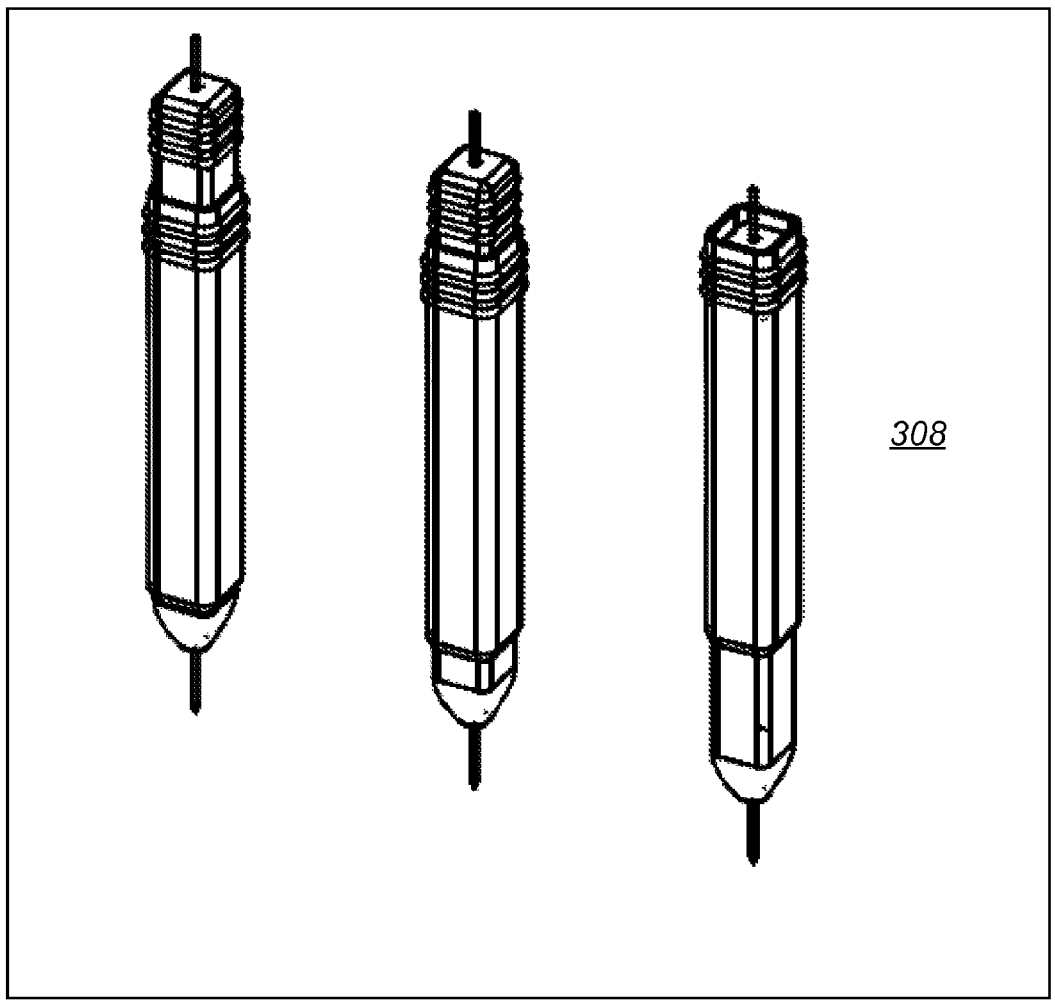
FIG. 12 is a schematic diagram of step 308 of the procedure of FIG. 9 depicting a perspective view of the three guide K-wires with hollow dilators placed around the solid dilators.
Figure 13:
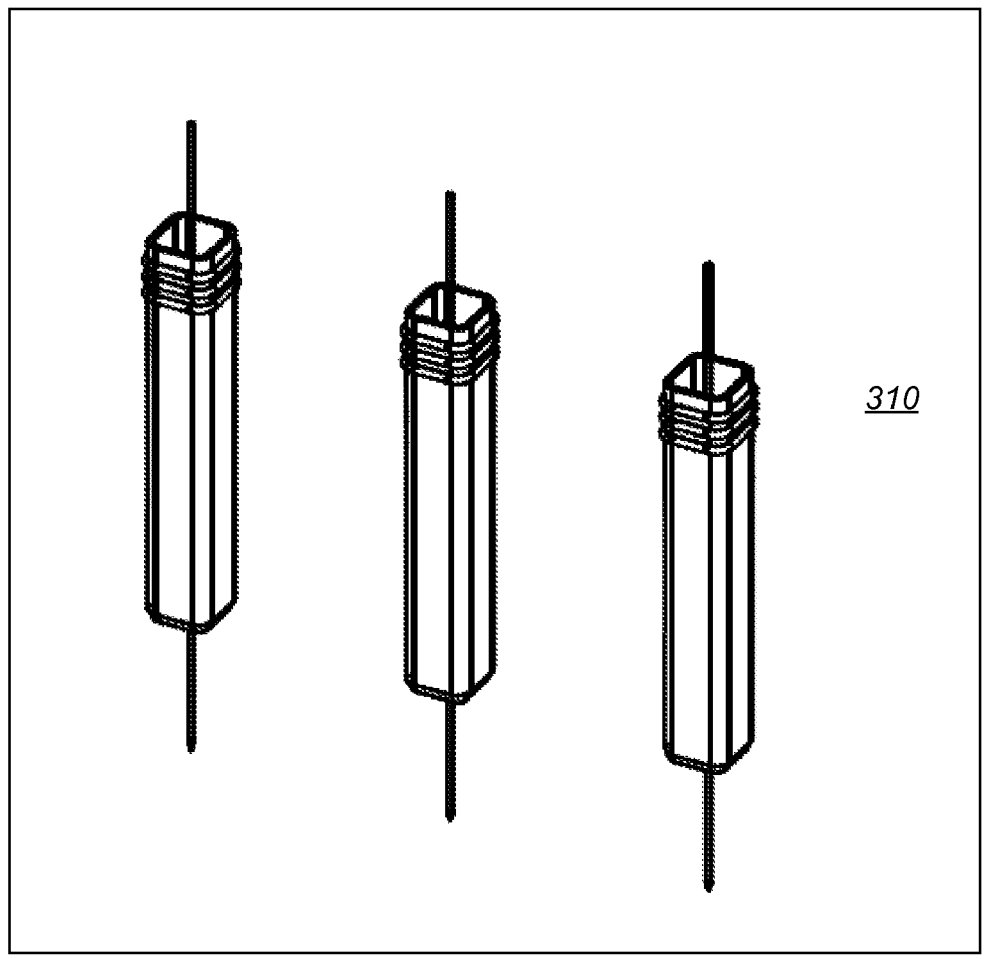
FIG. 13 is a schematic diagram of step 310 of the procedure of FIG. 9 depicting a perspective view of the three guide K-wires with the solid dilators removed.
Figure 14:
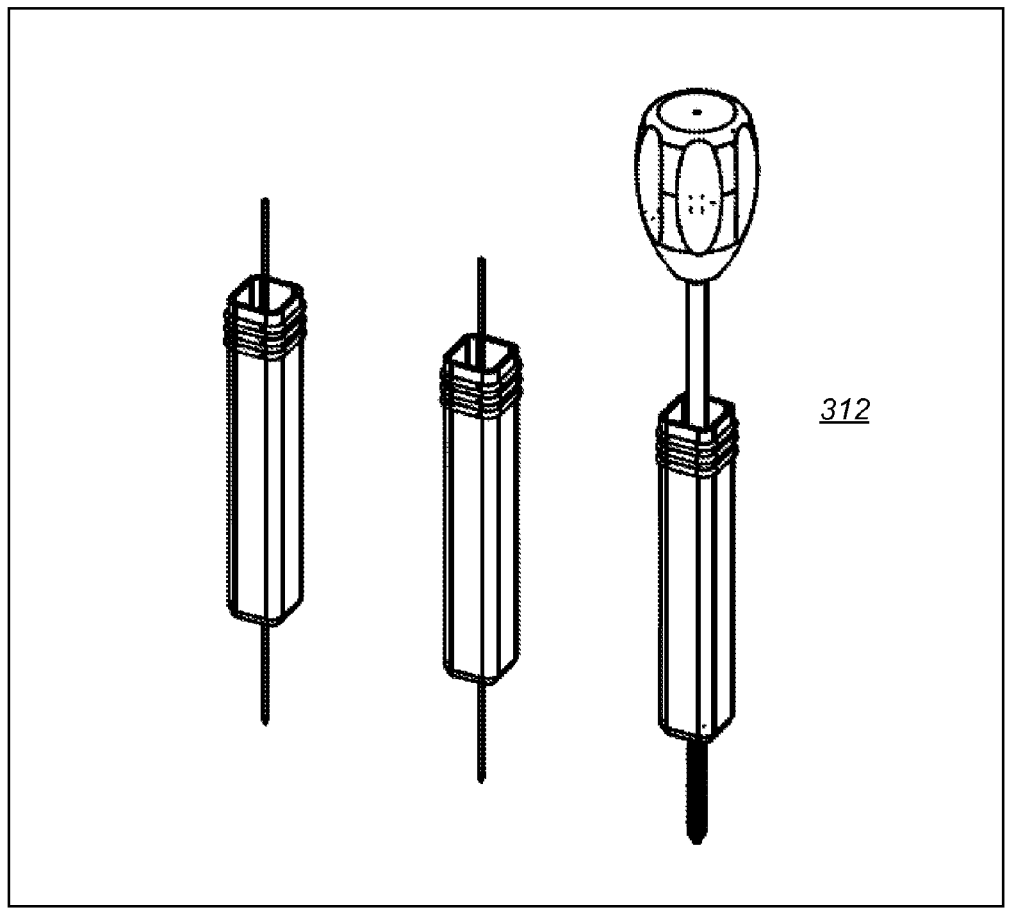
FIG. 14 is a schematic diagram of step 312 of the procedure of FIG. 9 depicting a perspective view of the three guide K-wires with a tapping tool placed over one of the guide wires for tapping the underlying pedicle.
Figure 15:
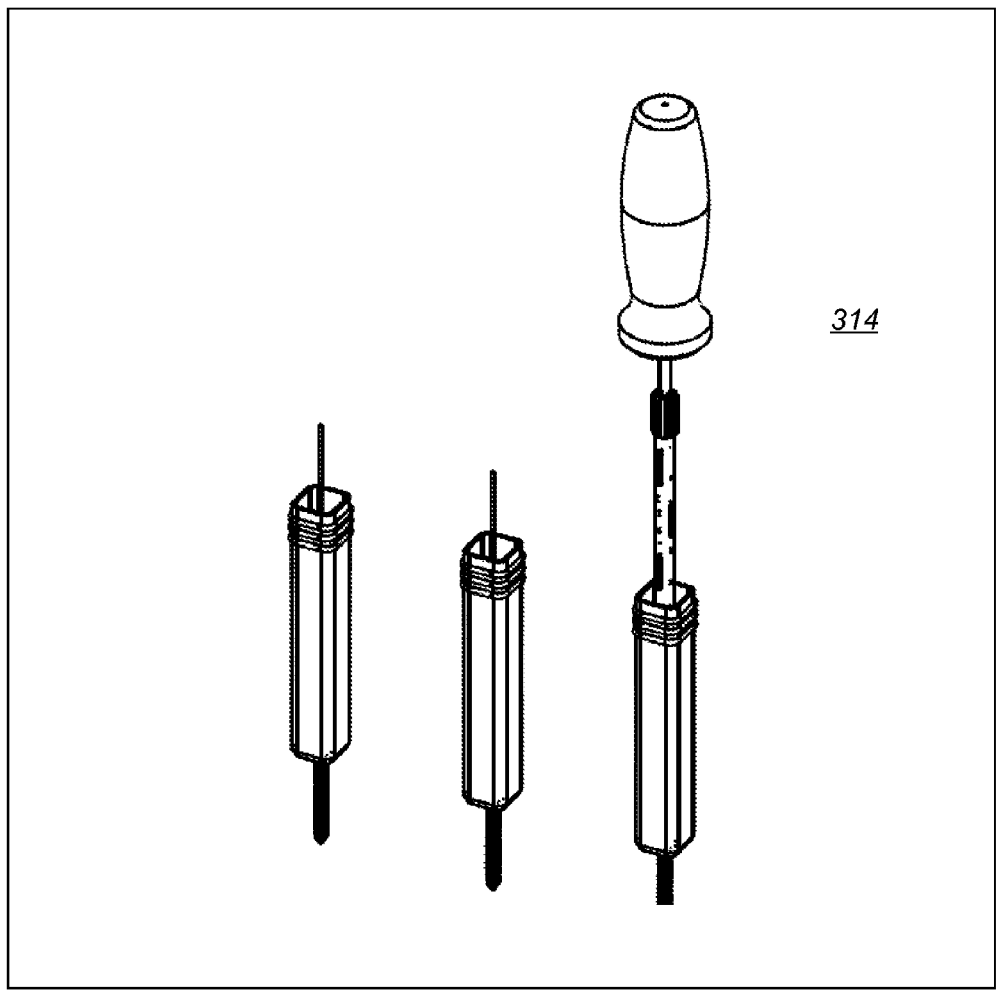
FIG. 15 is a schematic diagram of step 314 of the procedure of FIG. 9 depicting attaching a pedicle screw and a cage to the pedicle.
Figure 16:
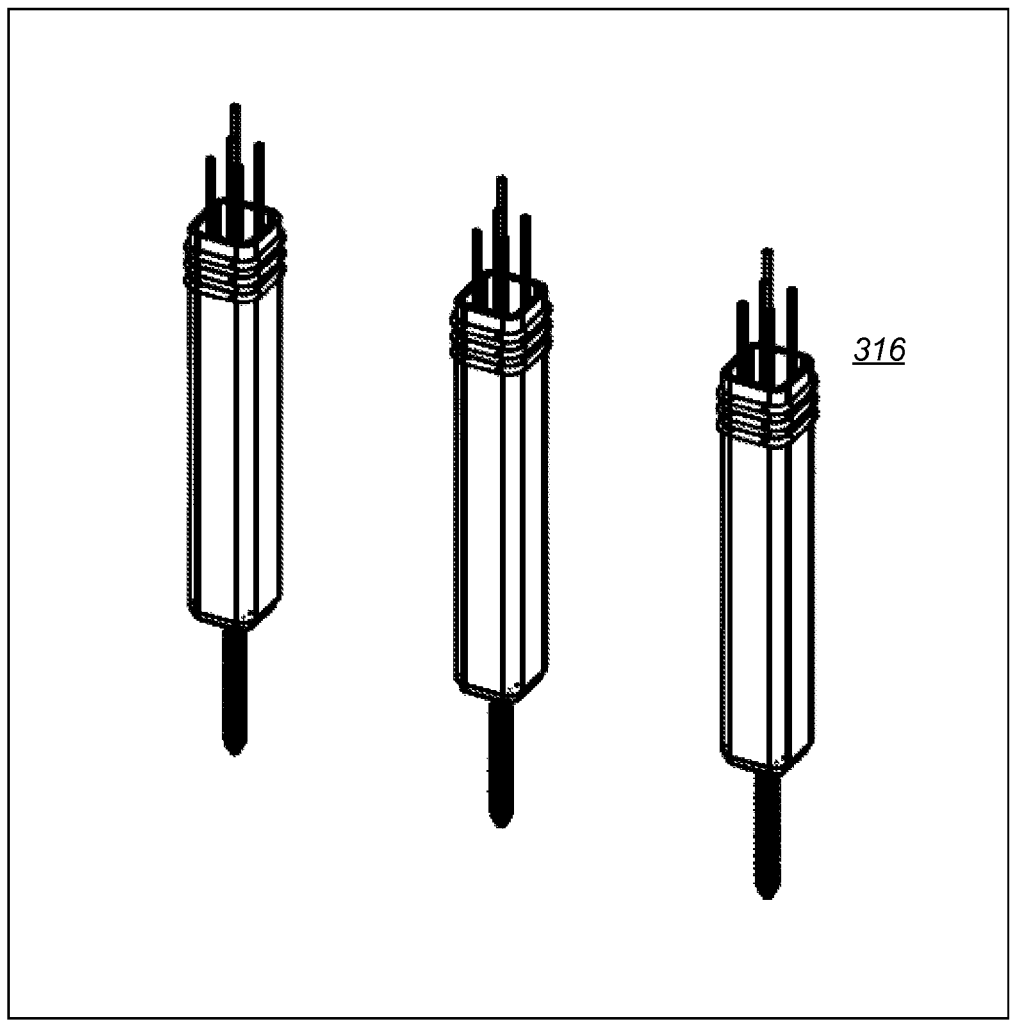
FIG. 16 is a schematic diagram of step 316 of the procedure of FIG. 9 depicting inserting of post wires into the cage bores.
Figure 17:
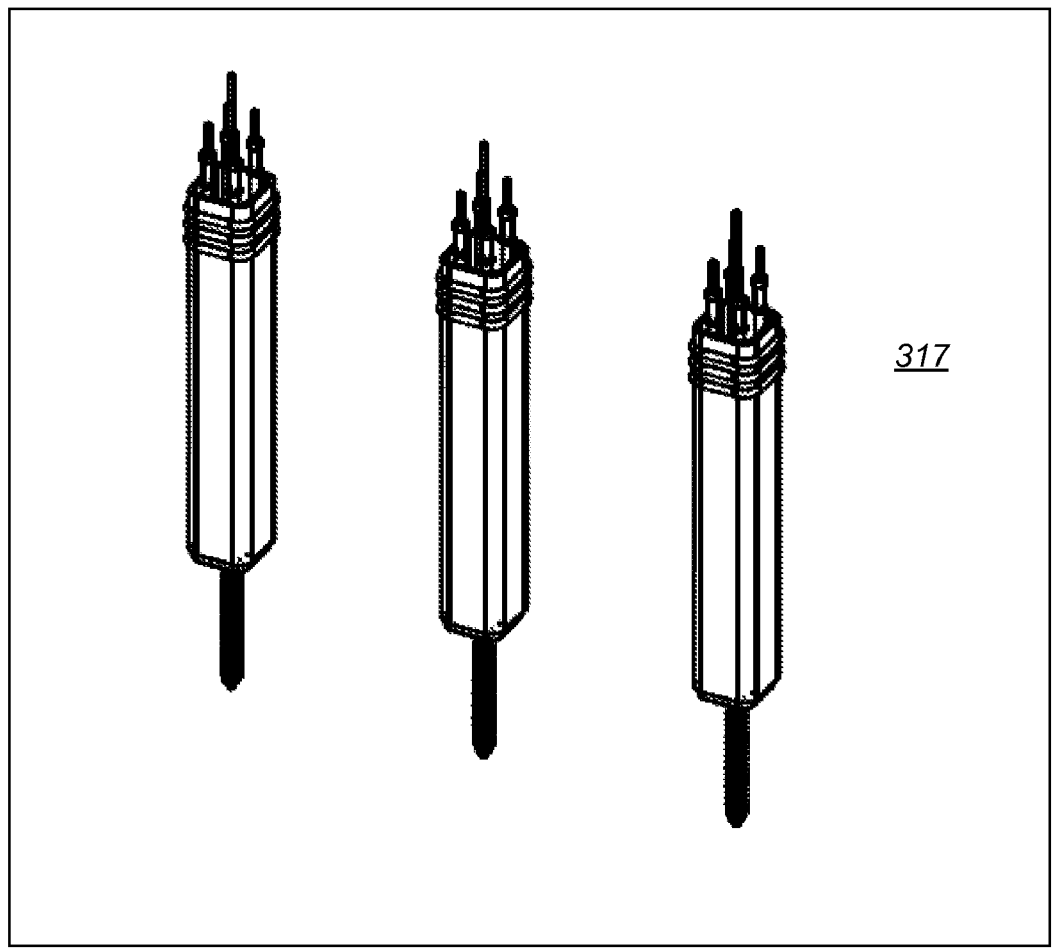
FIG. 17 is a schematic diagram of step 317 of the procedure of FIG. 9 depicting inserting posts along the post wires.
Figure 18:
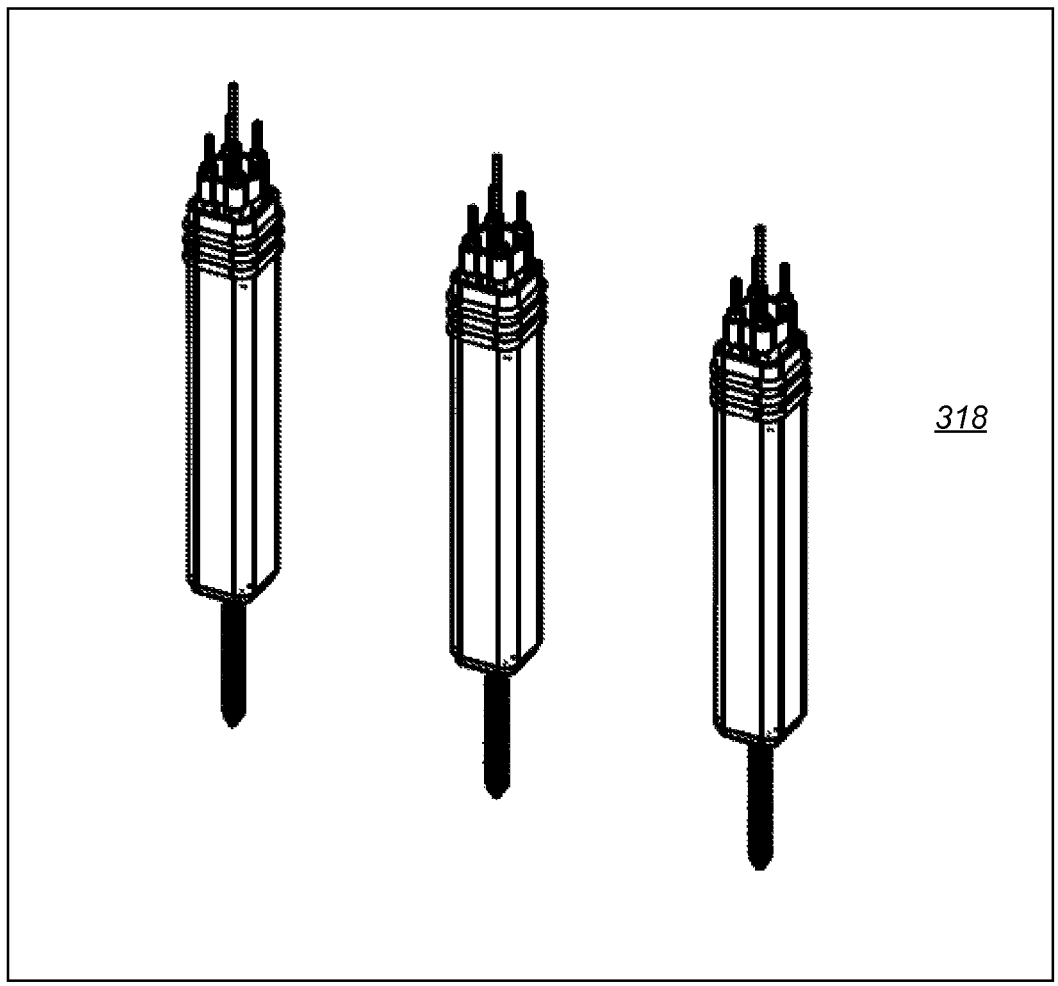
FIG. 18 is a schematic diagram of step 318 of the procedure of FIG. 9 depicting placing of a support ring over the posts.
Figure 19:
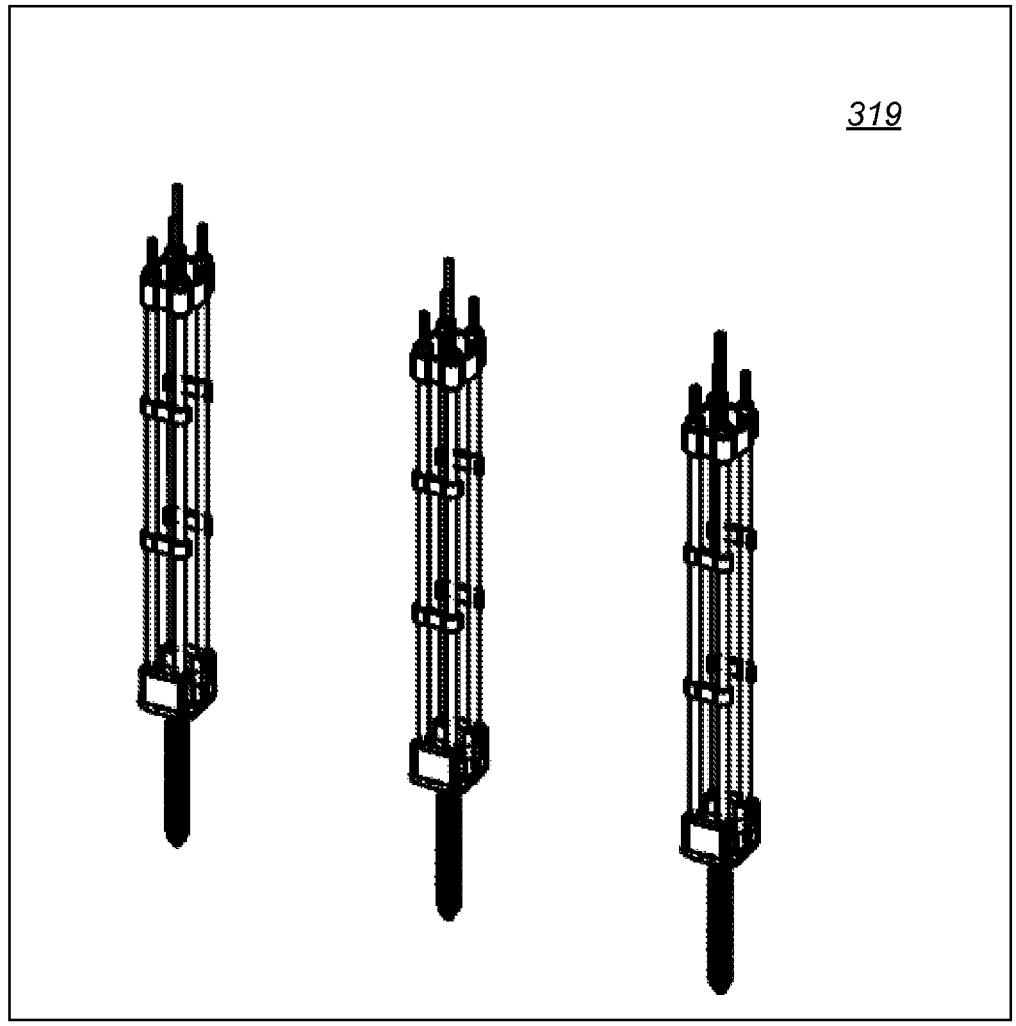
FIG. 19 is a schematic diagram of step 319 of the procedure of FIG. 9 with the hollow dilators removed.
Figure 20:
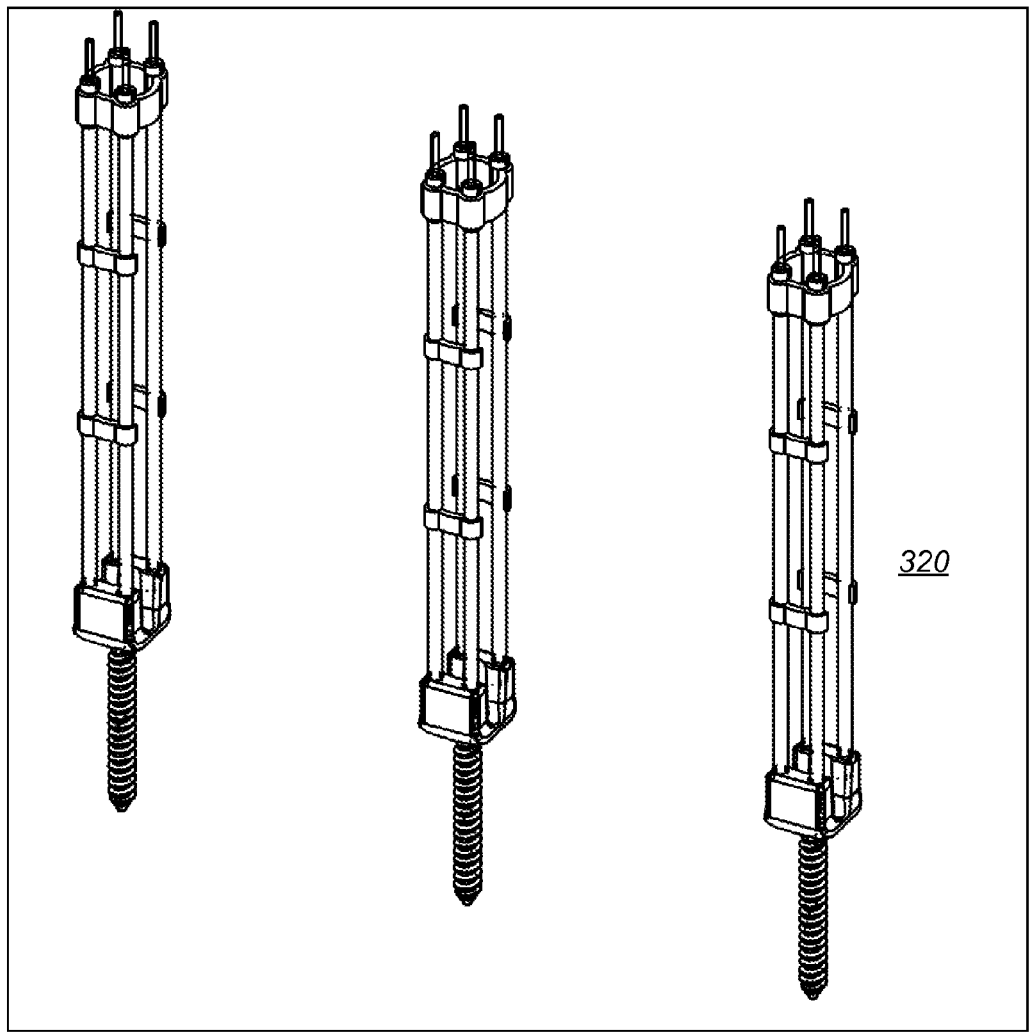
FIG. 20 is a schematic diagram of step 320 of the procedure of FIG. 9 with the guide wires removed.
Figure 21:
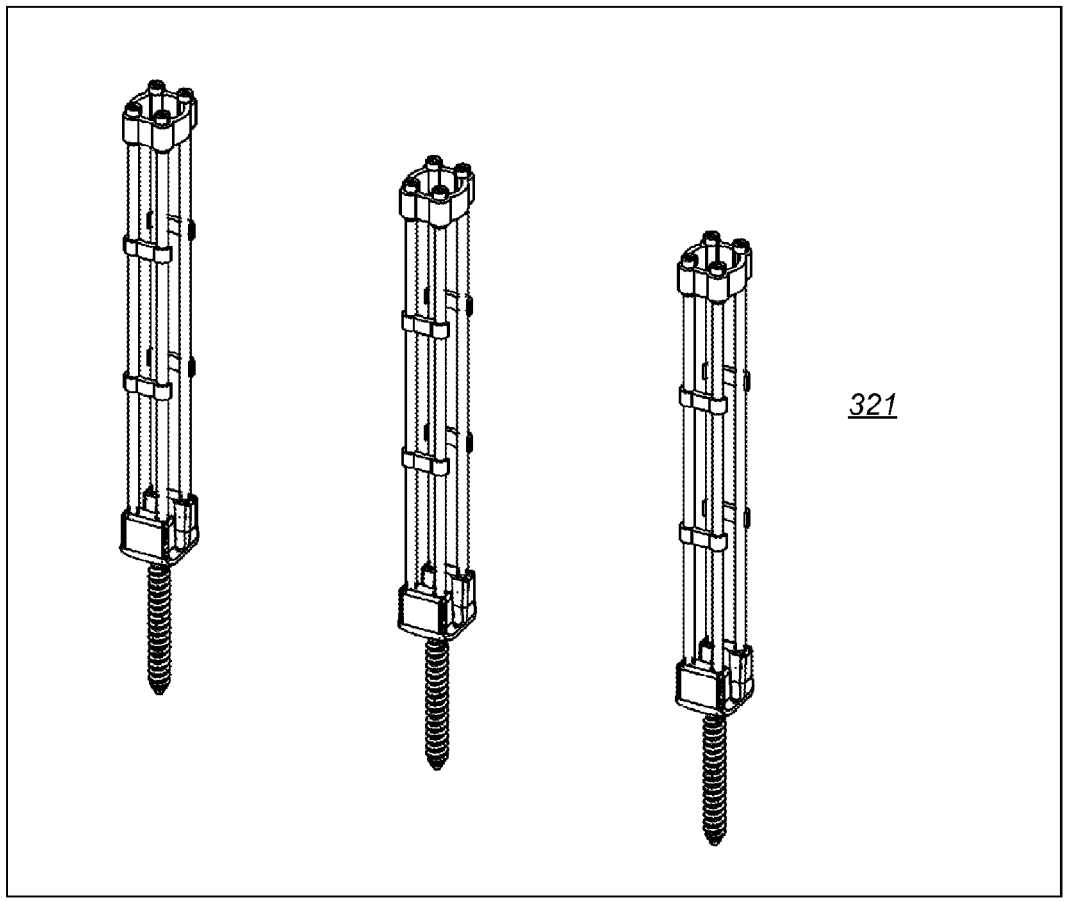
FIG. 21 is a schematic diagram of step 321 of the procedure of FIG. 9 with the post wires removed.
Figure 22:
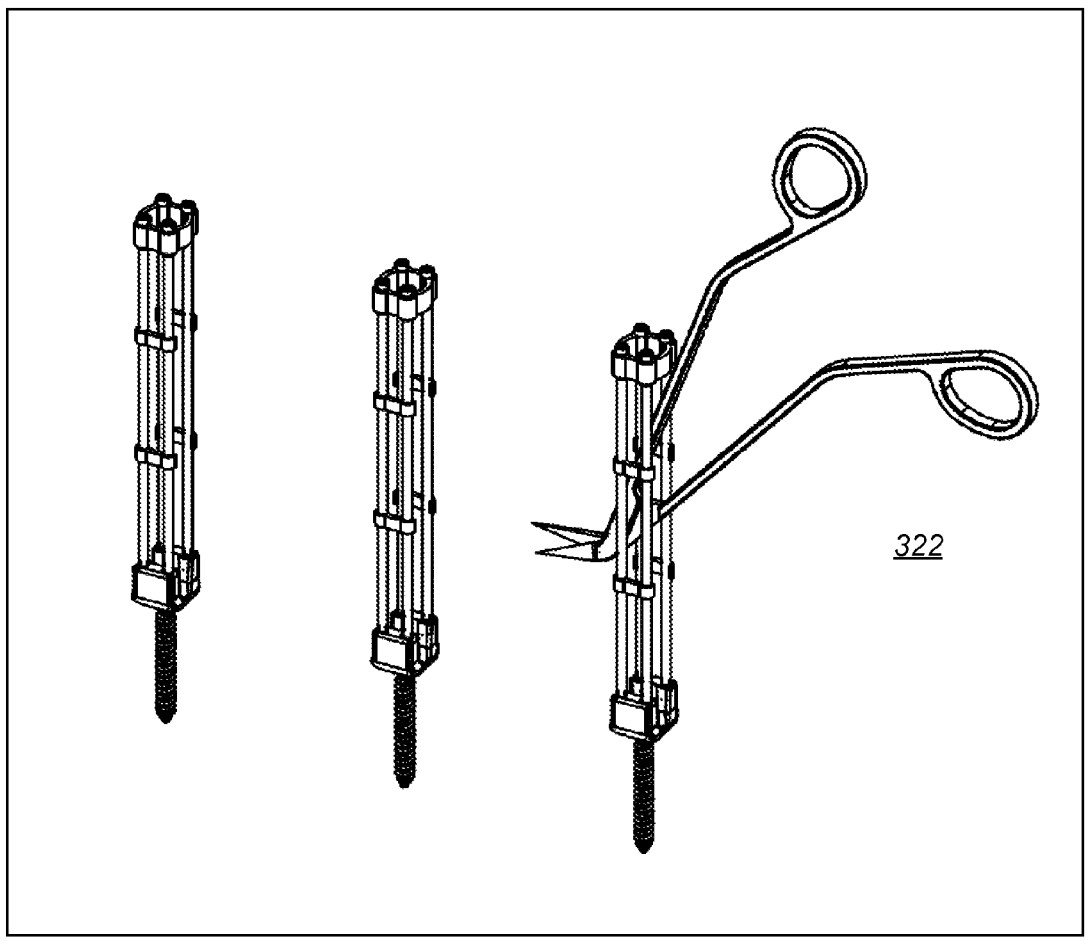
FIG. 22 is a schematic diagram of step 322 of the procedure of FIG. 9 depicting a perspective view of the three access devices and fascia clipping tool inserted into one of the access devices.
Figure 23:
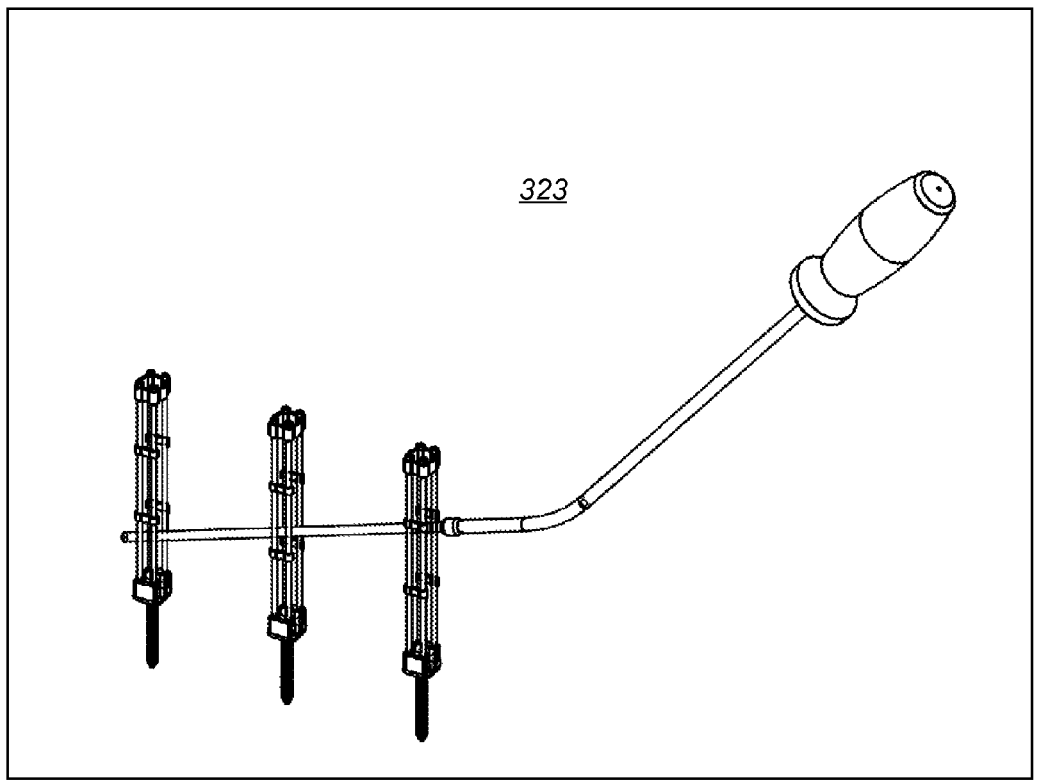
FIG. 23 is a schematic diagram of step 323 of the procedure of FIG. 9 depicting the insertion of a connecting rod through a channel formed by the posts of the access devices.
Figure 24:
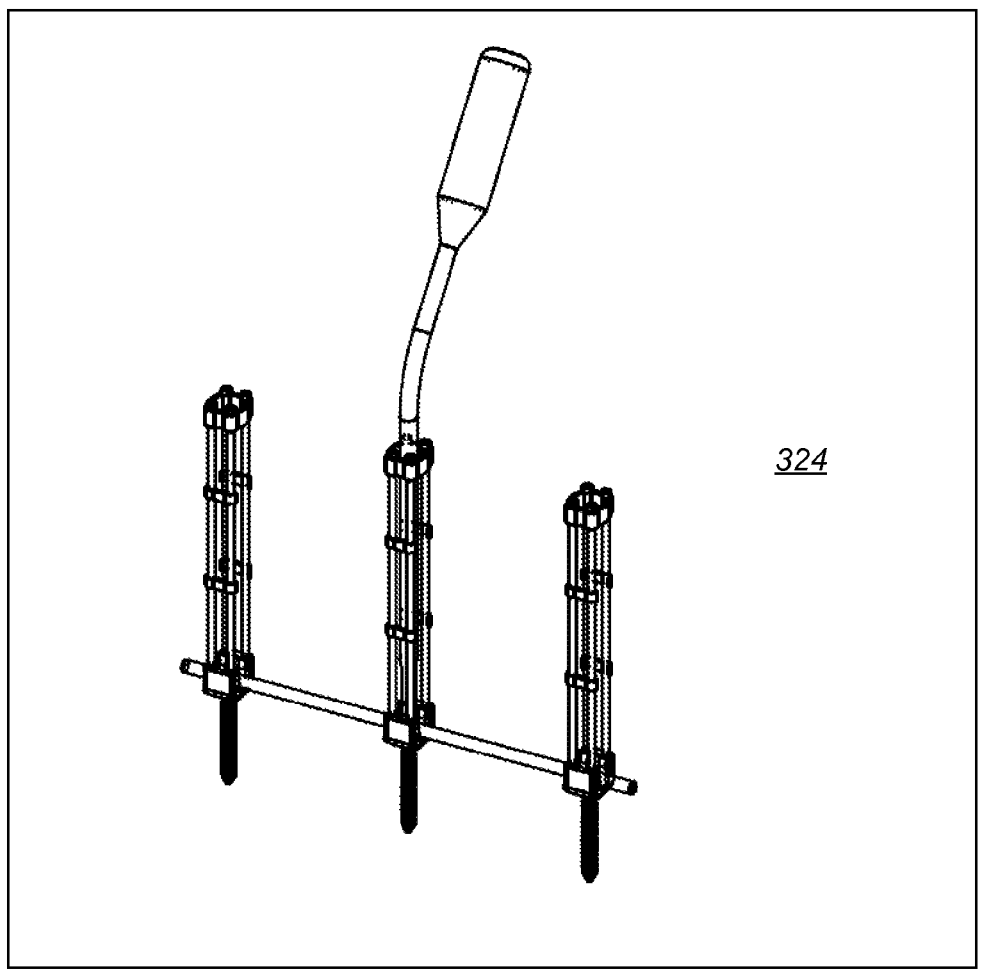
FIG. 24 is a schematic diagram of step 324 of the procedure of FIG. 9 depicting the pushing of the rod into the cage.
Figure 25:
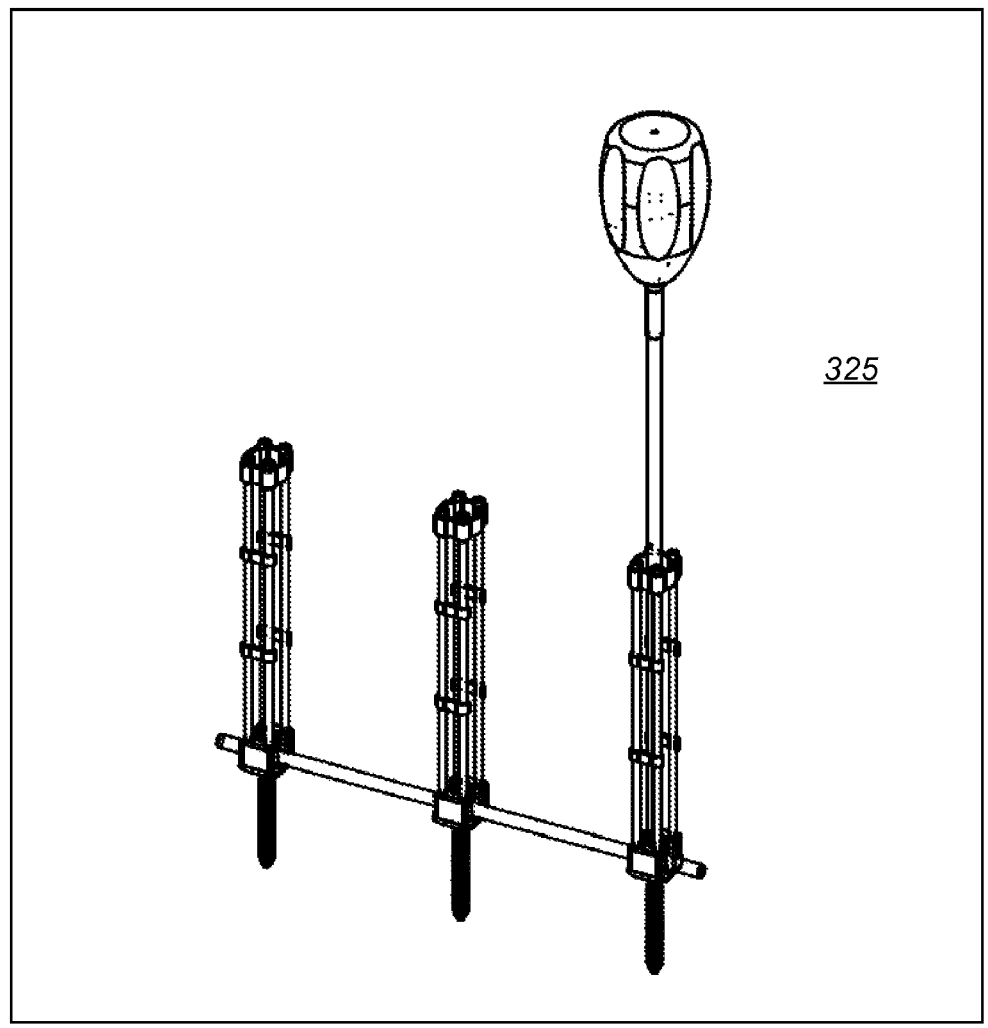
FIG. 25 is a schematic diagram of step 325 of the procedure of FIG. 9 depicting the tightening of the set screws.
Figure 26:
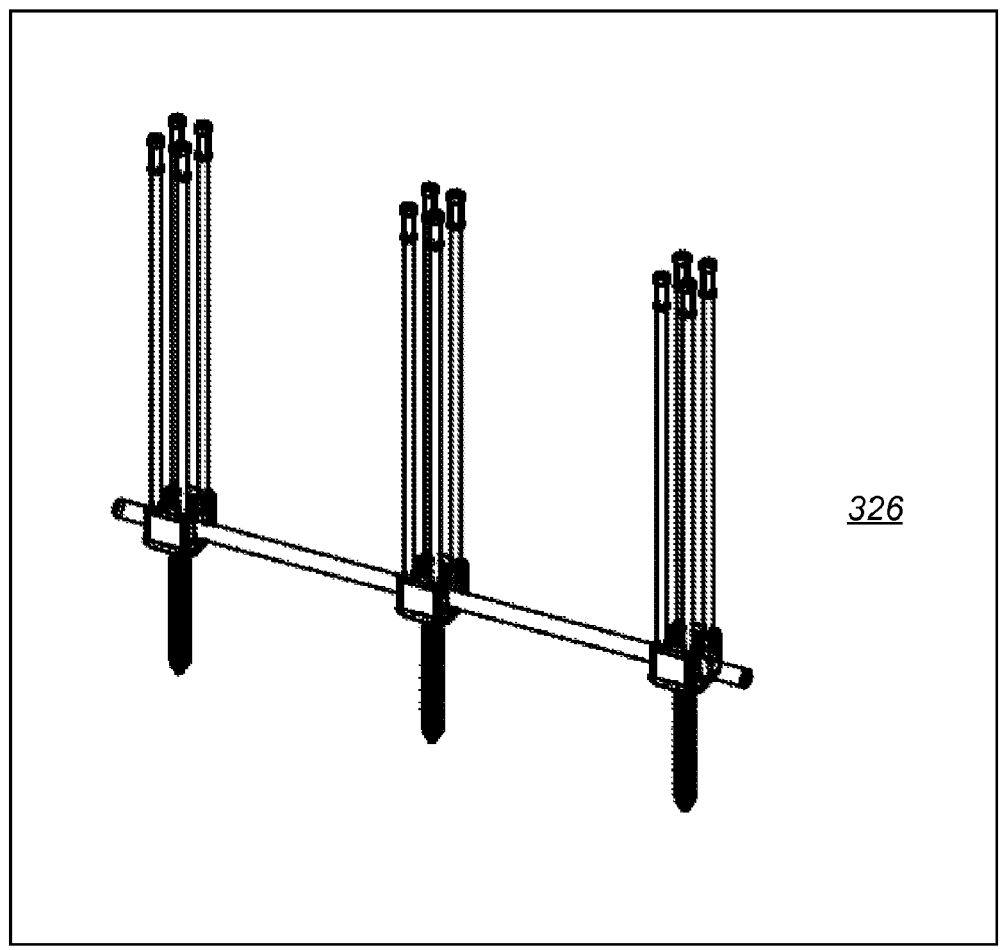
FIG. 26 is a schematic diagram of step 326 of the procedure of FIG. 9 with the support rings and snap-rings removed.
Figure 27:
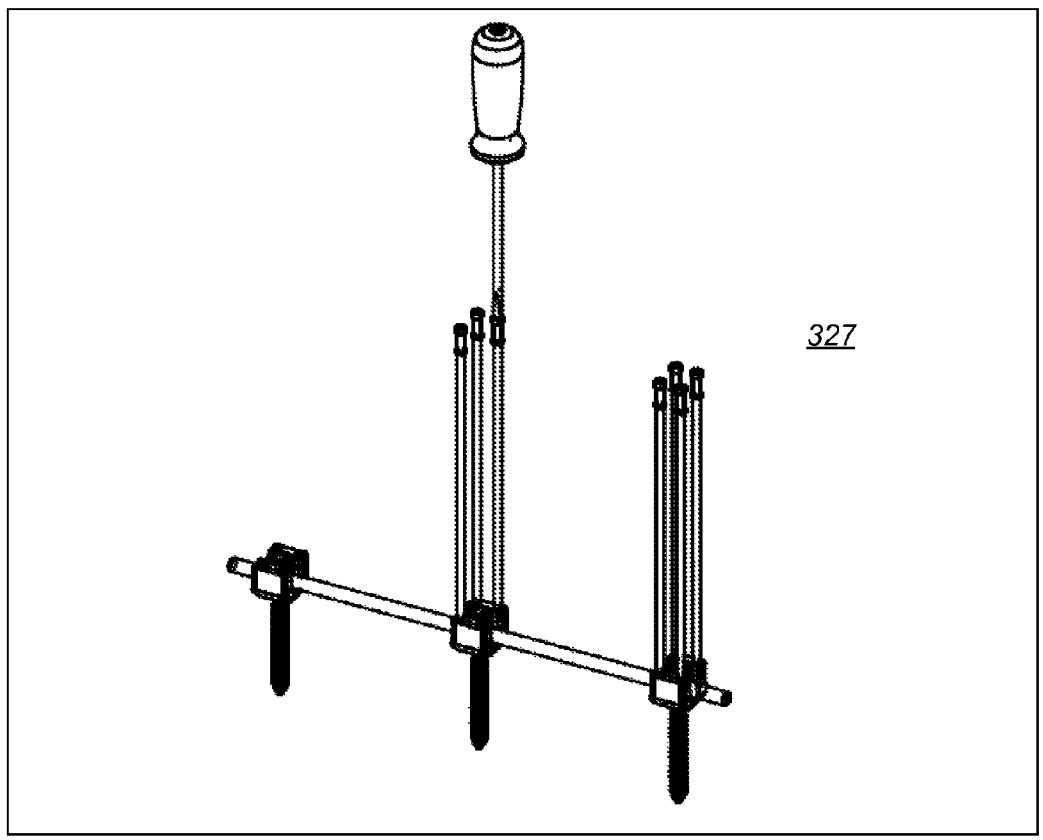
FIG. 27 is a schematic diagram of step 327 of the procedure of FIG. 9 depicting the removal of the posts.
Figure 28:
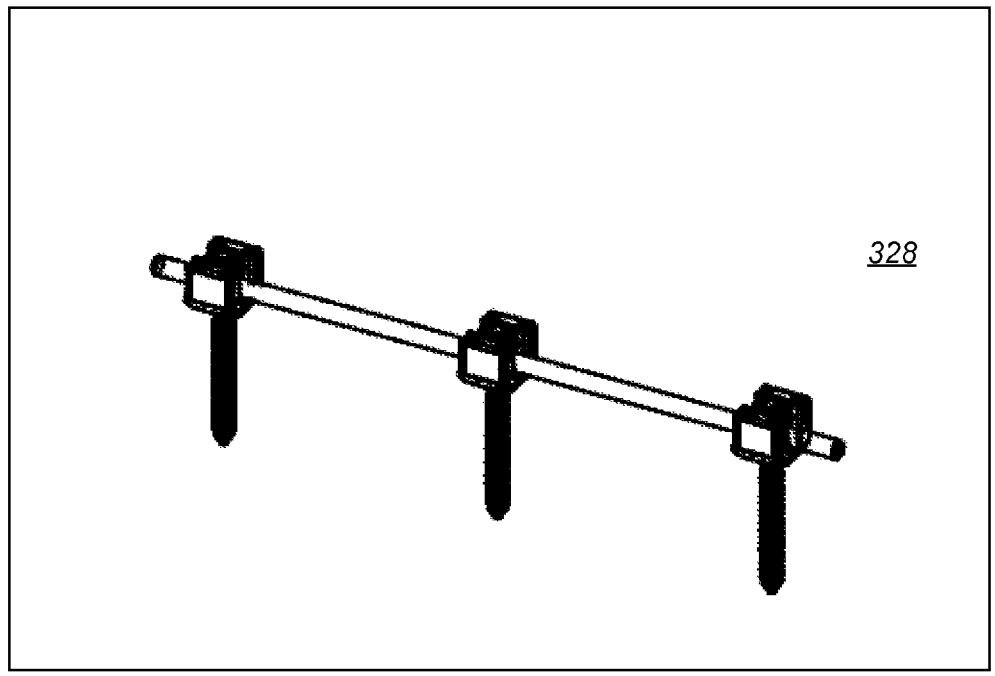
FIG. 28 is a perspective view of the final state of the installed rod and three pedicle screws assembly.
Figure 29:
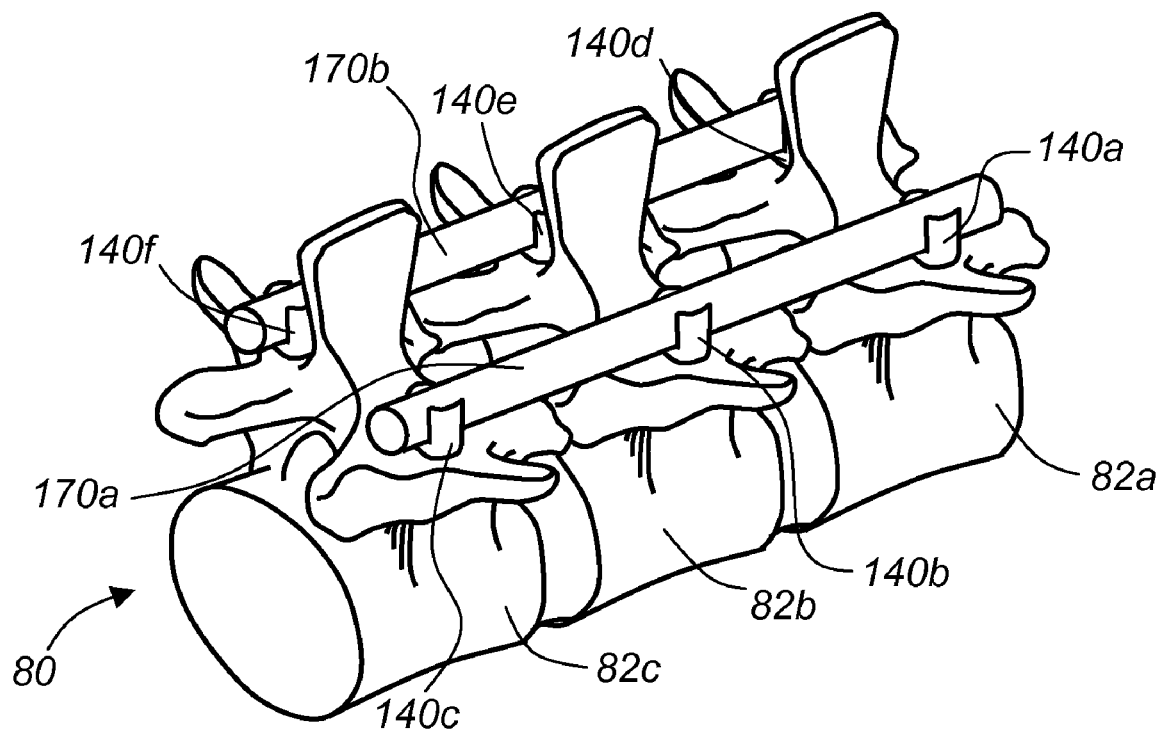
FIG. 29 is a perspective view of three adjacent vertebrae stabilized with connecting rods and pedicle screws according to the procedure of FIG. 9.
Figure 31:
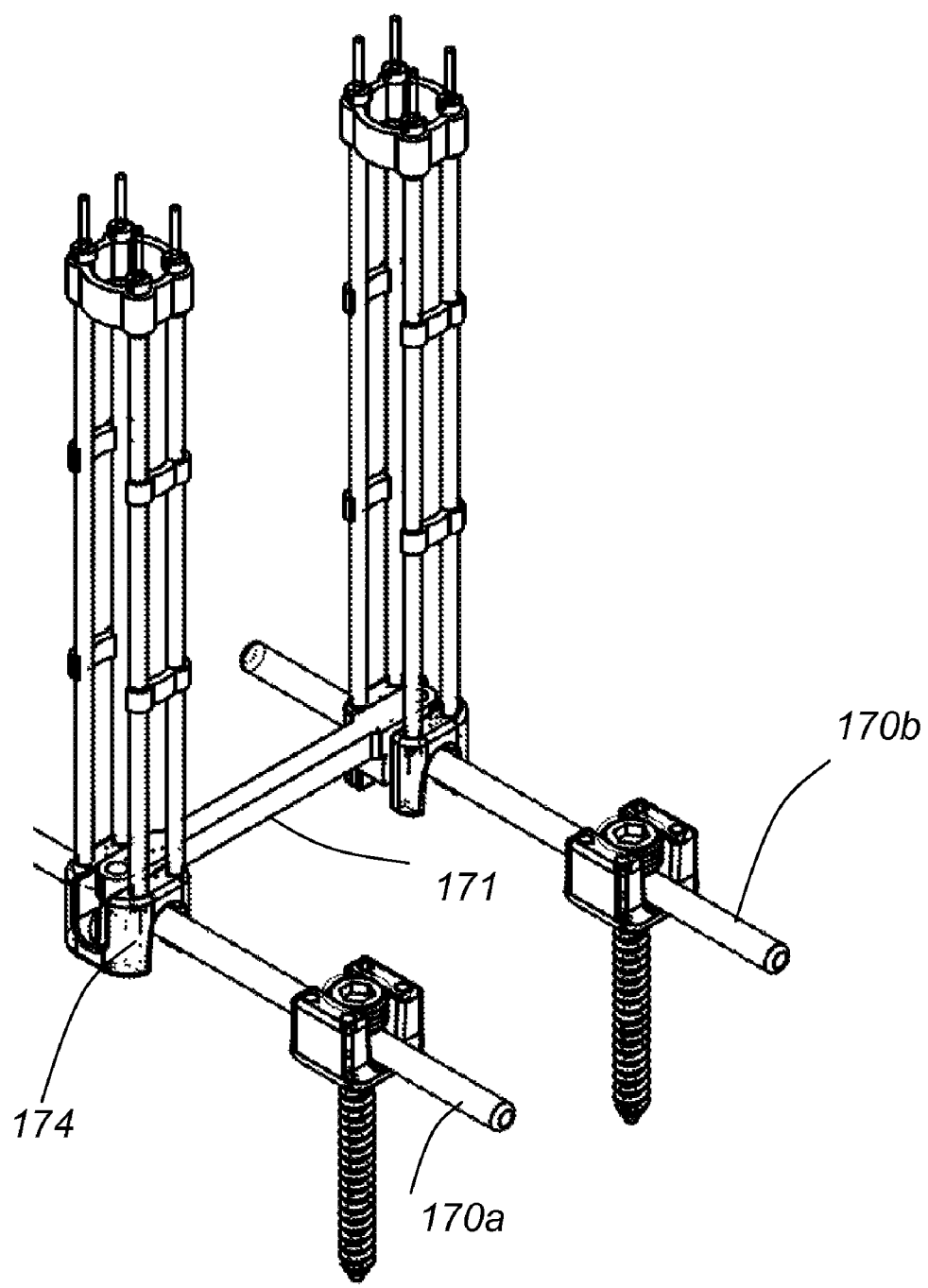
FIG. 31 is a perspective view of two installed stabilization rods in the X-direction and placement of a transverse stabilization rod in the Y-direction with the MIS access device of this invention.
Figure 32:
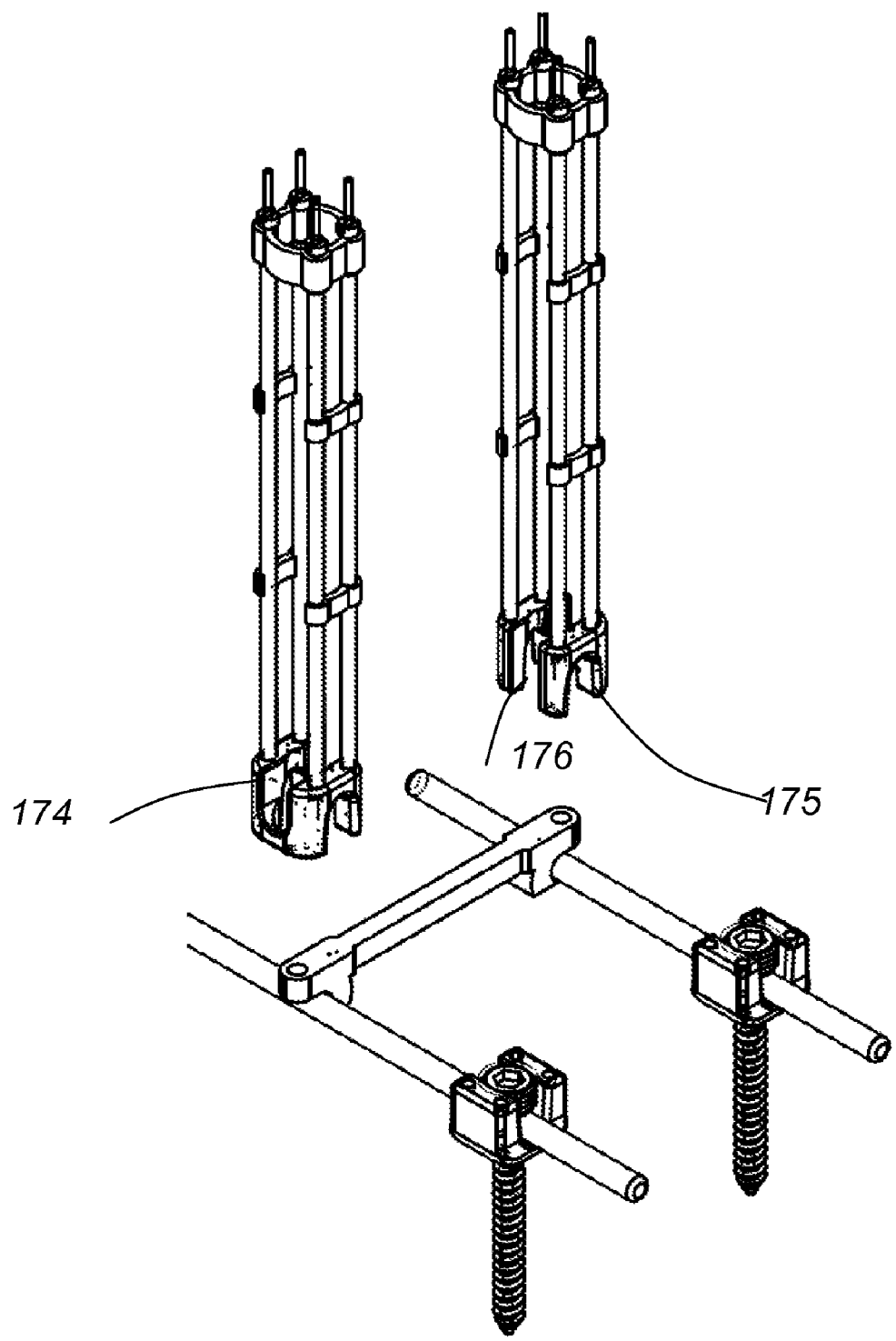
FIG. 32 is a perspective view of two installed stabilization rods in the X-direction and a transverse stabilization rod in the Y-direction.

Referring to FIG. 9, and FIG. 10-30, the process of implanting a stabilization device between two adjacent vertebrae includes the following steps. First the surgeon performs small skin incisions on the patient's body, as shown in FIG. 2, and forms skin openings (302). Next, the surgeon inserts guide K-wires through the skin openings into the underlying tissue and bones and anchors them in the pathology areas (304), as shown in FIG. 3 and FIG. 10. In one example, the pathology areas are the pedicles of the adjacent vertebrae. Next, the surgeon uses solid tissue dilators over the guide wires to open deep channels from the skin openings to the pathology areas (306), shown in FIG. 11. Next, he slides hollow dilators over the solid dilators (308), shown in FIG. 12, and then removes the solid dilators (310) (FIG. 13). Next, he taps the pedicles with the pedicle screw tap (312) (FIG. 14). Next, he removes the pedicle screw tap, inserts the cages with the protruding pedicle screws and drives the pedicle screws into the pedicles with a screw driver (314) (FIG. 15). Then, he inserts post wires into the hollow dilators and into the cage bores (316) (FIG. 16). Next, he inserts posts along the post wires and screws them into the cage bores (317) (FIG. 17). Next, he places a support ring on top of the four posts and two snap-rings between two adjacent posts in each hollow dilator (318) (FIG. 18). Then, he removes the hollow dilators (319) (FIG. 19), the guide wires (320) (FIG. 20), and the post wires (321) (FIG. 21). Next, he dissects and cuts the fascia between the access devices (322) (FIG. 22). Next he inserts a rod into the channel formed by the posts of the access devices (323) and places the rod within the cages of the access devices (FIG. 23). Next, he pushes the rod with a pusher tool down into the cage base (324) (FIG. 24), and then inserts and tightens the set screws onto the cage thereby securing the rod to the cage (325) (FIG. 25). Once the rod is secured, the surgeon removes the support ring and the snap rings from the access device posts (326) (FIG. 26). Finally, he unscrews the access device posts from the cage, removes them from the patient's body (FIG. 27) and closes the incisions (327). The advantage of the post-type access device is that it allows insertion and placement of the stabilizing rod from any direction between the four posts without having to rotate, remove and reinsert the access device during the operation. The screw can also be placed while rotating with the access device or separately from the access device. The lack of any solid sides also allows improved visualization of the tissues and the screws and rod. There is also the option to assemble the access device outside of the patient's body and then place the screw with the access device inside the patient's body. This is the first system that allows placement of wires inside the cage of a pedicle screw. This is also the first system that places cannulated posts inside the cage of a pedicle screw. The snap-on connectors are also unique features that provide stability to the posts for taller constructs above 5 cm. Stabilizing rods 170a, 170b may be placed between adjacent vertebrae 82a, 82b, 82c either in linear configuration (shown in FIG. 29), H-shape or X-shape configurations. Stabilizing rods may also be placed laterally 171, i.e., extending from pedicle screw 140c to 140f of FIG. 29 or extending from rod 170a to rod 170b, as shown in FIGS. 31 and 32. This is the first system that allows placing crosslink rods 171 transverse to the longitudinal rods 170a, 170b, via an MIS procedure. Cage 174 of the MIS access device includes channels 175 and 176, oriented perpendicular to each other and dimensioned to accommodate the longitudinal rod 170a in the X-direction and the transverse rod 171 in the Y-direction, respectively.

Figure 30:
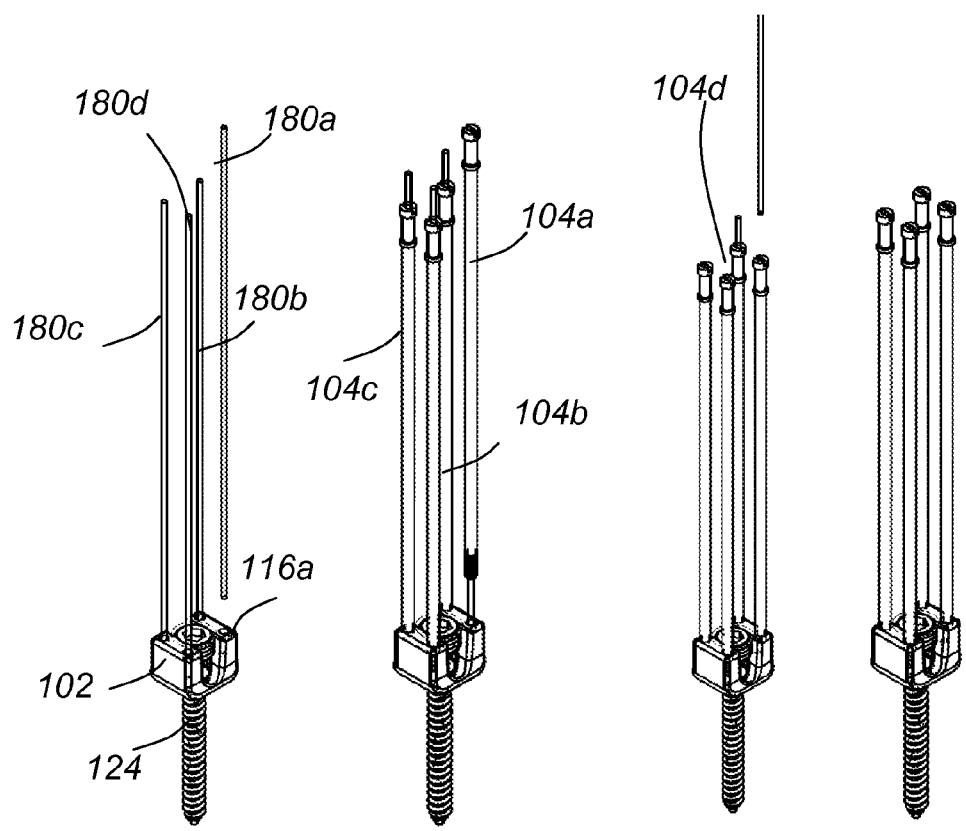
FIG. 30 is a detailed perspective view of the assembling procedure for the access device.

Referring to FIG. 30, in another embodiment, four post wires 180a-180d, are inserted in the four bores 116a-116d of the cage 102. Next, the surgeon inserts the pedicle screw 124 into the aperture 114 of the cage base 112 and inserts the cage/four post wires/screw assembly into the patient. Next, the surgeon slides hollow posts 104a-104d over the post wires 180a-180d down into the bores and screws the hollow posts to the cage 102. Then he removes the post wires 180a-180d, leaving the hollow posts in place. This embodiment allows the pedicles screws to be placed and attached to the pedicles without the access device.

Other embodiments are within the scope of the following claims. For example, the cage and/or the support ring may have other cross-sections such as triangular, rectangular, square, oval or polygonal. The number of posts may be two, three, four or more than four. The stabilizing device may be a rod, wire or a plate. The stabilizing devices may be placed in x, y, or any other direction within the x-y plane or at an angle to x-y plane. The devices may be made of metal such as stainless steel, titanium, plastic, rubber, graphite, glass, expandable materials under body temperature, or other radiolucent materials. The access device may be preassembled outside of the patient's body and then inserted into the patient's spinal locations or it may be assembled inside the patient's body, as was described above.

Several embodiments of the present invention have been described. Nevertheless, it will be understood that various modifications may be made without departing from the spirit and scope of the invention. Accordingly, other embodiments are within the scope of the following claims.

What is claimed is:

1. A system for providing access to a spine of a patient, the system comprising a post-type access device insertable into a first location of the patient's spine said access device comprising:
   a cage comprising a bottom portion configured to receive a bone fixation element and prevent the bone fixation element from passing entirely therethrough and first and second side portions extending from said bottom portion parallel to each other and forming a channel configured to receive a spine stabilization element and a locking element, wherein receipt of the locking element by the side portions causes locking of the relative positions of the bone fixation element and the stabilization element;
   first and second elongated posts extending from said first side portion and third and fourth elongated posts extending from said second side portion and wherein said elongated posts are arranged to permit passage of said stabilization element along any direction transverse to a central axis of the access device;
   a support ring attached to proximal ends of said elongated posts; and
   a first semi-ring configured to be attached to and connect said first and second elongated posts along a direction transverse to said central axis, and a second semi-ring configured to be attached to and connect said third and fourth elongated posts along a direction transverse to said central axis.

2. The system of claim 1 further comprising one or more additional post-type access devices insertable into the patient's spine in locations adjacent to said first location.

3. The system of claim 1 wherein said bone fixation element comprises a polyaxial screw.

4. The system of claim 1 wherein said spine stabilization element comprises a rod.

5. The system of claim 1 wherein said bone fixation element comprises a screw.

6. The system of claim 1 wherein said elongated posts are arranged to permit passage of objects along said transverse direction or said central axis, and wherein said objects are selected from a group consisting of carrier devices, surgical instruments, medical devices, fixation devices, vertebral disc replacement devices, facet arthroplasty devices, vertebral element replacement devices, interbody devices, fixation tools, connecting devices, connecting tools, tissue, grafting material, and illumination devices.

7. The system of claim 1 wherein said elongated posts are cannulated.

* * * * *